(12) United States Patent
Andreoli et al.

(10) Patent No.: US 6,734,012 B2
(45) Date of Patent: May 11, 2004

(54) LOW FLUORESCENCE NYLON/GLASS COMPOSITES FOR MICRO-ANALYTICAL DIAGNOSTIC APPLICATIONS

(75) Inventors: Rita Andreoli, Thomaston, CT (US); Murtaza Amin, Sykesville, MD (US); Mark Meyering, Middlefield, CT (US); Richard Chesterson, Orange, CT (US); Eugene Ostreicher, Farmington, CT (US)

(73) Assignee: Cuno Incorporated, Meriden, CT (US)

( * ) Notice: Subject to any disclaimer, the term of this patent is extended or adjusted under 35 U.S.C. 154(b) by 0 days.

(21) Appl. No.: 09/899,607

(22) Filed: Jul. 5, 2001

(65) Prior Publication Data

US 2002/0119559 A1 Aug. 29, 2002

Related U.S. Application Data

(60) Provisional application No. 60/224,141, filed on Aug. 10, 2000, provisional application No. 60/216,390, filed on Jul. 6, 2000, and provisional application No. 60/216,229, filed on Jul. 5, 2000.

(51) Int. Cl.[7] .............................. C12M 1/34; C12Q 1/00; C12Q 1/68; C12N 11/00; C12N 11/08
(52) U.S. Cl. .......................... 435/287.1; 435/4; 435/6; 435/174; 435/180
(58) Field of Search ............................. 435/4, 6, 287.1, 435/174, 180

(56) References Cited

U.S. PATENT DOCUMENTS

| | | | |
|---|---|---|---|
| 3,874,986 A | 4/1975 | Browall et al. | 161/160 |
| 3,876,738 A | 4/1975 | Marinaccio et al. | 264/41 |
| 4,473,474 A | 9/1984 | Ostreicher et al. | 210/636 |
| 4,473,475 A | 9/1984 | Barnes, Jr. et al. | 210/638 |
| 4,645,602 A | 2/1987 | Barnes, Jr. et al. | 210/490 |
| 4,707,265 A | 11/1987 | Barnes, Jr. et al. | 210/638 |
| 4,711,793 A | 12/1987 | Ostreicher et al. | 427/244 |
| 4,837,162 A | 6/1989 | Rothman et al. | 435/331 |
| 4,921,878 A | 5/1990 | Rothman et al. | 521/53 |
| 5,006,287 A | 4/1991 | Davis | 264/41 |
| 5,062,691 A | 11/1991 | Tristani-Kendra et al. | 359/56 |
| 5,124,128 A | 6/1992 | Hildenbrand et al. | 422/59 |
| 5,420,047 A | 5/1995 | Brandt et al. | 435/7.9 |
| 5,667,976 A | 9/1997 | Van Ness et al. | 435/6 |
| 5,760,130 A | 6/1998 | Johnston et al. | 525/54.2 |
| 5,919,626 A | 7/1999 | Shi et al. | 435/6 |
| 6,056,529 A | 5/2000 | Meyering et al. | 425/143 |
| 6,387,631 B1 | 5/2002 | Arnold et al. | 435/6 |

FOREIGN PATENT DOCUMENTS

| | | |
|---|---|---|
| EP | 0 605 828 A1 | 7/1994 |
| EP | 0 614 987 A | 9/1994 |
| WO | WO 01/61042 A2 | 8/2001 |

OTHER PUBLICATIONS

ASTM (American Society for Testing and Materials)—Designation: E 1294–89 (Reapproved 1999) Standard Test Method for Pore Size Characteristics of Membrane Filters Using Automated Liquid Porosimeter—This test method uses the automated bubble point method described in ASTM Test Method F316, pp. 1 and 2 of 2.

"Analysis of the Fluroescent and Phosphorescent Species in Nylon–6,6 in Relation to Aldol Condensation Products of Cyclopentanone" by N. S. Allen and M. J. Harrison, Eur. Polym. J. vol. 21, No. 6, pp. 517–526, 1985.

*Primary Examiner*—David M. Naff
(74) *Attorney, Agent, or Firm*—R. Thomas Payne; John A. Tomich

(57) ABSTRACT

An improved combination non-luminescent microporous membrane and solid support for use in micro-analytical diagnostic applications is disclosed. Specifically, composite microarray non-luminescent slides having a microporous membrane effectively attached by covalent bonding through a surface treatment to a substrate that prepares the substrate to sufficiently, covalently bond to the non-luminescent microporous membrane formed by a phase inversion process such that the combination produced thereby is useful in microarray applications and wherein the porous non-luminescent nylon composite microarray slides are covalently bonded to a solid base member, such as, for example, a glass or Mylar microscope slide, such that the combination produced thereby is useful in microarray applications. Apparatus and methods for fabricating lithe non-luminescent composite microarray slides are also disclosed.

19 Claims, 14 Drawing Sheets

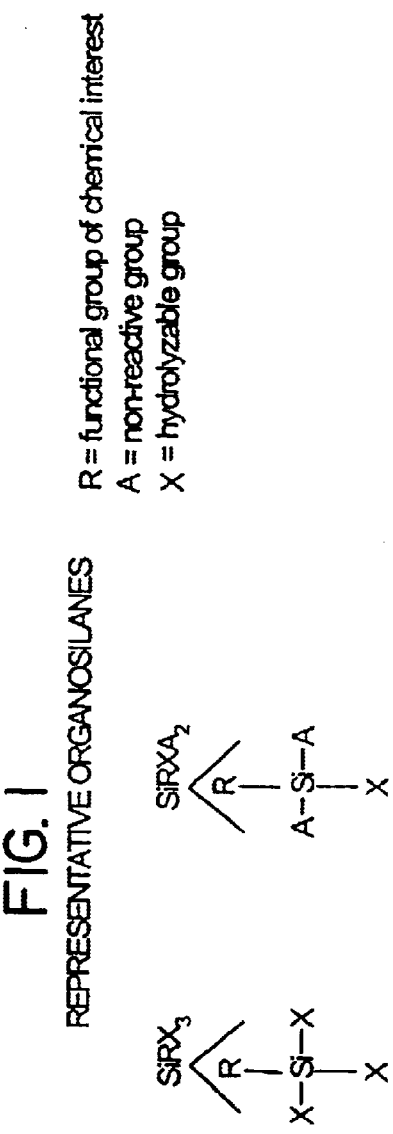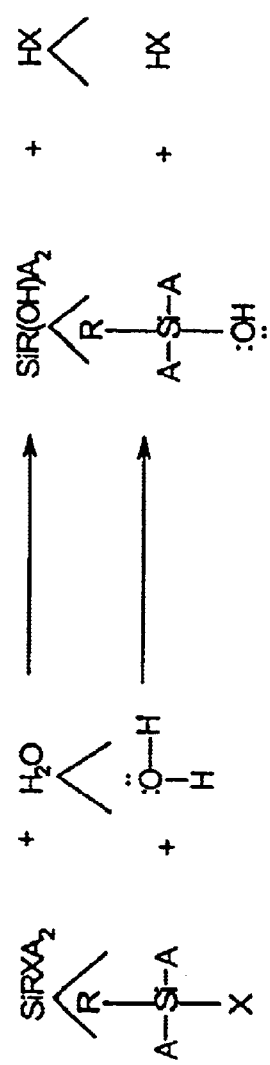

SILANOL CONDENSATION REACTION

FIG. 4
REACTIONS OF EPOXY GROUPS
A: With an amine group
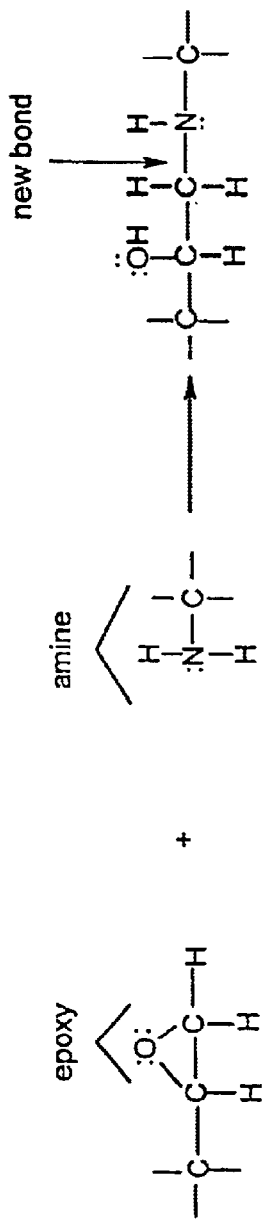
B: With a carboxyl group
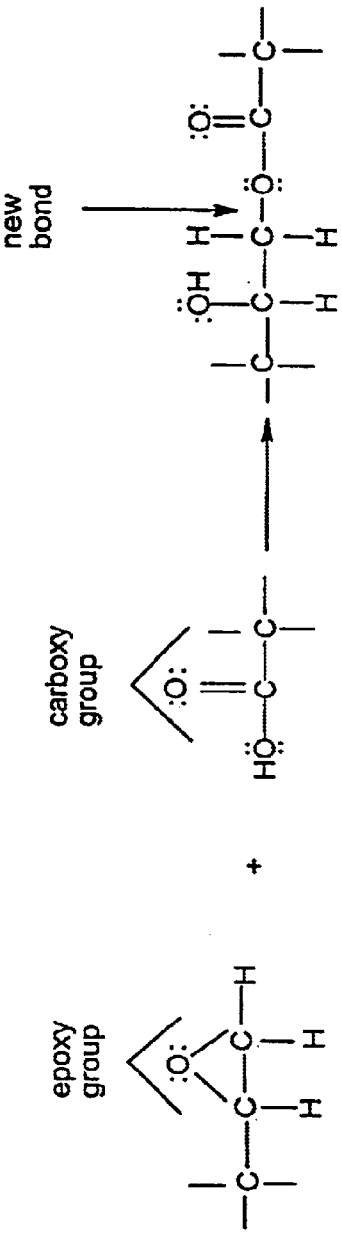

Bond using 3-Amino propyl triethonysilane and polyamido polamine epichlorohydrin polymer.

Bond using 10-carbomethoxy-decyl-dimethyl chlorosilane and polyamido polyamine epichlorohydrin polymer.

Bond using glycidoxypropyl trimethoxysilane

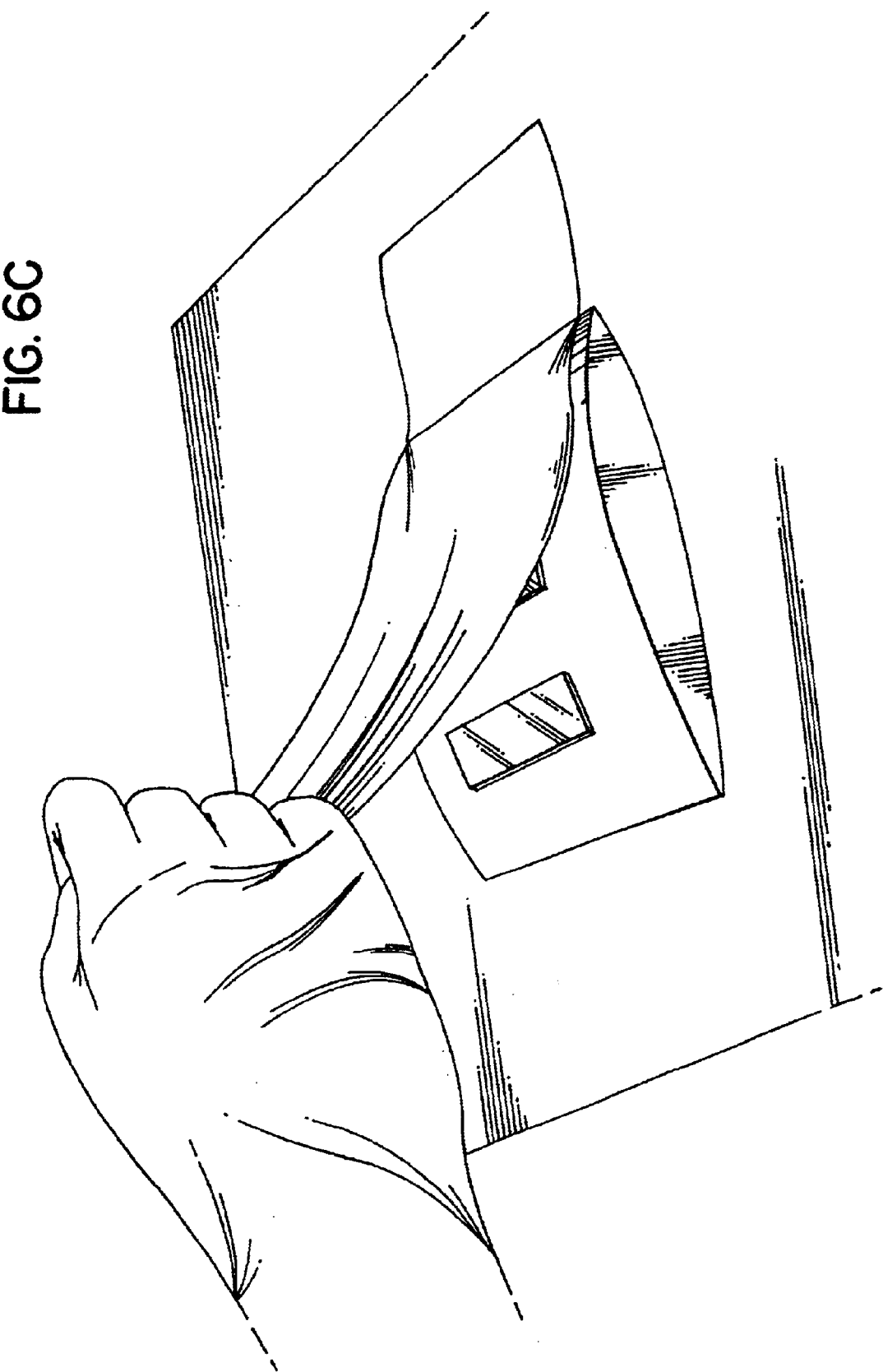

LOW FLUORESCENCE NYLON/GLASS COMPOSITES FOR MICRO-ANALYTICAL DIAGNOSTIC APPLICATIONS

RELATED APPLICATIONS

This application is a continuation-in-part of commonly owned U.S. Provisional Patent Application Serial No. 60/224,141, entitled "Improved Low Fluorescence Nylon/Glass Composites for Micro-Analytical Diagnostic Applications" of Ostreicher et al., filed Aug. 10, 2000, and is related to commonly owned U.S. Provisional Patent Application Serial No. 60/216,229, entitled "IMPROVED NON-LUMINESCENT SUBSTRATE" of Rita J. Andreoli, filed Jul. 5, 2000, and U.S. Provisional Patent Application Serial No. 60/216,390, entitled "Improved Combination of Microporous Membrane and Solid Support for Micro-Analytical Diagnostic Applications" of M. Amin et al., filed Jul. 6, 2000, the disclosure of each is herein incorporated by reference to the extent not inconsistent with the present disclosure.

BACKGROUND OF THE DISCLOSURE

The present disclosure relates to composite microarray non-luminescent slides useful for carrying a microarray of biological polymers on the surface thereof and, more particularly, to composite microarray non-luminescent slides having a microporous membrane effectively attached by covalent bonding through a surface treatment to a substrate that prepares the substrate to sufficiently, covalently bond to the microporous membrane formed by a phase inversion process such that the combination produced thereby is useful in microarray applications and, most particularly, to composite microarray non-luminescent slides having a porous nylon membrane covalently bonded to a solid base member, such as, for example, a glass or Mylar microscope slide, such that the combination produced thereby is useful in microarray applications and to a process for producing such composite microarray non-luminescent slides.

A variety of methods is currently available for making arrays of biological macromolecules, such as, for example, arrays of nucleic acid molecules or proteins. One method for making ordered arrays of DNA on a porous membrane is a "dot blot" approach. In this method, a vacuum manifold transfers a plurality, e.g., 96, aqueous samples of DNA from three (3) millimeter diameter wells to a porous membrane. A common variant of this procedure is a "slot-blot" method in which the wells have highly-elongated oval shapes.

The DNA is immobilized on the porous membrane by baking the membrane or exposing it to UV radiation. This is a manual procedure practical for making one array at a timer and usually limited to 96 samples per array. "Dot-blot" procedures are therefore inadequate for applications in which many thousand samples must be determined.

A more efficient technique employed for making ordered arrays of genomic fragments (e.g., PCR products) uses an array of pins dipped into the wells, e.g., the 96 wells of a microtitre plate, for transferring an array of samples to a substrate, such as a porous membrane. One array includes pins that are designed to spot a membrane in a staggered fashion, for creating an array of 9216 spots in a 22×22 cm area (Lehrach, et al., 1990). A limitation with this approach is that the volume of DNA spotted in each pixel of each array is highly variable. In addition, the number of arrays that can be made with each dipping is usually quite small.

Several patents have described the use of microarray slides in microarray applications. These include U.S. Pat. No. 5,919,626 entitled, "Attachment of unmodified nucleic acids to silanized solid phase surfaces"; U.S. Pat. No. 5,667,976 entitled, "Solid supports for nucleic acid hybridization assays" and U.S. Pat. No. 5,760,130 entitled "Aminosilane/carbodiimide coupling of DNA to glass substrate", the disclosure of each is herein incorporated by reference to the extent not inconsistent with the present disclosure.

Microarray slides are well known in the art. Schleicher & Schuell have attempted to attach nylon membrane to a glass slide using glue or similar adhesive in their commercially available CAST™ slides. However, the layer of glue or adhesive adds additional thickness to the nylon membrane/glass slide combination, and the gluing/adhesive process may require the use of a scrim-reinforced nylon membrane. The extra thickness of the overall nylon membrane/glass slide combination caused by the glue/adhesive and the reinforcing scrim is a disadvantage in microarray applications. Additionally, the scrim makes the surface of the membrane of the nylon membrane/glass slide combination uneven and less than ideal from a cosmetic standpoint. Even further, the chemistry of the glue or adhesive used to attach the nylon membrane to the glass slide is not necessary optimal to effectuate the combination, nor is it necessarily compatible with the biomolecules or analytes for which the product is intended to receive, as it may interfere or react with the analyte.

Similarly, other products known to be currently commercially available include: Modified glass that binds nucleic acids or proteins without the use of a membrane; Corning GAPS Slides, such as, for example CMT-GAPS™ coated slides; Nitrocellulose porous membrane cast onto glass, available from Schleicher & Schuell as FAST™ Slides; Scrim-reinforced nylon glued or adhered to a glass substrate and Schleicher & Schuell CAST™ Slides. Detailed descriptions of these commercially available products are readily available from the respective manufacturer and are known in the art.

However, in microarray applications, binding nucleic acids or proteins directly to a glass substrate has certain disadvantages. Specifically, a considerably smaller surface area for binding the nucleic acids or proteins is available than with a comparably sized microporous membrane/glass slide combination. The larger the binding surface area the, better the signal strength of the biomolecules or analytes, thereby allowing for the detection of smaller samples of biomolecules or analytes. Also, the porous membrane portion of the microporous membrane/glass slide combination naturally adsorbs the biomolecules or analytes and holds them in place on the microporous membrane/glass slide combination, whereas without the microporous membrane portion of the slide, the biomolecules or analytes would just sit on top of a glass surface, as there is no adsorption of the biomolecules or analytes. It is also likely that the efficiency of immobilization of biomolecule on the glass is substantially less than 100%, and may be less than 50%, when compared to immobilization of the target on nylon. This is important, in that the subsequent detection steps require as much of the possible analyte, or target biomolecule, to be available for (in a DNA detection example) hybridization with the labeled probe. Following the immobilization, there are typically several liquid immersion steps including blocking, washing, hybridization buffer exposure, etc. Each step has the potential of removing analyte from the glass surface, and decreasing the potential strength of the signal. Nylon is generally regarded as having the highest biomolecule binding efficiency when compared to other the commercially available polymer or other treated substrates. Nylon is also regarded as providing highest accessibility of the functional groups of the analyte thus bound to the nylon surfaces.

Nylon membranes, a specific species of microporous membrane, formed by a phase inversion process, have some advantages over nitrocellulose membranes in that nylon is naturally hydrophilic. Nylon membranes also have a greater protein and DNA binding capacity than nitrocellulose. This increased binding capacity means better signal strength and lower detection thresholds in assays.

Nylon membrane pore structure is more easily controllable than nitrocellulose membrane pore structure and is more physically robust than the nitrocellulose membranes. Nitrocellulose is more brittle than the nylon membrane, has more pore variability and is extremely flammable. The physical weakness, variability and flammability of the nitrocellulose membranes combine to make nitrocellulose membrane more expensive to manufacture than nylon membrane.

As discussed above, there are at least three main disadvantages to scrim-reinforced nylon glued or otherwise adhered to a glass substrate. First, the glue or adhesive layer adds additional thickness to the combination scrim-reinforced nylon/glass slide. The arraying robots that blot the nylon membranes have narrow spatial tolerances, and any additional thickness represents additional uncertainty about accurate positioning of the combination scrim-reinforced nylon/glass slide relative to the arraying robots. The second, and more important, disadvantage is that the scrim-reinforced membrane on the combination scrim-reinforced nylon/glass slide has an irregular surface on the micro scale. This is an important cosmetic problem since the spot sizes made on the membrane are on a similar scale. Finally, the glue/adhesive and the analyte may not be compatible. Specifically, the adhesive which contains an excess of functionalized moieties for attachment can indiscriminatiely bind the analyte in a way which makes it unavailable for detection; either by binding to the molecule preventing (in the DNA example) hybridization, or by reversibly binding to the analyte such that the attachment is not permanent, and the analyte is sloughed off in the liquid immersion steps prior to detection. Finally, the adhesive itself can be degraded in the multi-step processes leading to detection, and become, by extraction or other means, a mobile species. The adhesive fragment, if bound to the analyte, may be displaced to a location or area beyond the location of detection, or itself become part of a false background signal, depending on the type of detection being performed.

In these types of microarray slides, it is useful to have a nylon microporous layer that is flat, uniform, and is as thin as possible. In the case of charge modified slides, the degree of charge modification must be uniform over the entire slide surface. In the environment of use, as envisioned for the innovative slide's described in the present application, the bond between the nylon and the base member, such as, for example, a glass slide or Mylar sheet, must remain stable in water, NaOH, sodium dodecyl sulfate, and other harsh chemicals for prolonged periods of time and at high temperatures. Because of the high air pressure generated between the nylon membrane layer and the glass substrate when the nylon membrane is wetted, the bond therebetween must also be physically strong.

Further, it would be desirable to use fluorescent assays, as opposed to isotopic assays, if the detection sensitivity of fluorescent assays could be enhanced without increasing the potential for undesired chemical reactions. While sensitivity can be increased if the substrate on which fluorescent assays are performed does not fluoresce upon such exposure, isolation of such substrates having widespread usefulness (with respect to numerous analytes) has so far eluded the art.

Specifically, great varieties of assay systems have been developed to detect the presence and concentration of analytes in samples. For example, bioaffinity and enzymatically activated catalysis reactions are widely used in medicine and science to analyze biological samples to detect and quantitize biological materials of concern. Many of these assay systems depend upon the binding of one chemical entity with the material of concern (or a modified form thereof) and detection of the conjugate, e.g., antigen-antibody, nucleic acid strand to complementary nucleic acid strand ("hybridization"), and protein-ligand conjugates. The conjugate is typically detected by way of a label providing a detectable signal that is attached to one or more of the binding materials. The conjugate is frequently quantitated by first determining the amount of label in the free and bound fractions, and then calculating the amount present using an algorithm and a set of standards to which the samples are compared.

The most common labels used in analyte binding assays are radioisotopes and luminescent compounds. Luminescence is induced by energy transfer and refers to light emission that cannot be attributed merely to the temperature of the emitting body. Luminescent labels can be made to luminesce through photochemical (so-called, "photoluminescence"), chemical (so-called, "chemiluminescence") and electrochemical (so-called, "electrochemiluminescence") means. Photoluminescence, which includes fluorescence and phosphoresence, is a process whereby a material is induced to luminesce when it absorbs electromagnetic radiation such as visible, infrared or ultraviolet radiation. Chemiluminescence refers to luminescence occurring as a result of a chemical reaction without an apparent change in temperature. Electrochemiluminescence refers to luminescence occurring as a result of electrochemical processes.

Isotopic labeling proffers considerably better detection in certain analyte systems than luminescent labeling. For example, the most sensitive methods for detecting nucleic acids typically involve the use of isotopic labeling, often involving radiolabelling with $^{32}P$.

In localizing particular sequences within genomic deoxyribonucleic acid ("DNA"), a transfer technique described by Southern is typically employed. DNA is digested, often using one or more restriction enzymes, and the resulting fragments are separated according to size by electrophoresis through a gel. Conventionally the DNA is then denatured in situ and transferred from the gel to a solid support, the relative positions of the DNA fragments being preserved during and after the transfer to the solid support. The DNA attached to the solid support is then hybridized to radiolabelled DNA or ribonucleic acid ("RNA"), and autoradiography is used to locate the positions of bands complementary to the probe.

For many years, immobilization and hybridization of denatured DNA was carried out almost exclusively using nitrocellulose as a solid support. As time progressed, however, it became apparent that nitrocellulose was a less than an ideal solid-phase hybridization matrix, as nucleic acids are attached to the nitrocellulose support by hydrophobic, rather than by covalent, interactions, and the nucleic acids are released slowly from the matrix during hybridization and washing at high temperatures. To overcome this problem, charge-modified cellulose supports, including DBM(diazobenzyloxymethyl)-cellulose and APT-cellulose, were introduced in the early 1980's to provide improved nucleic acid binding. These matrices however, like nitrocellulose itself, also suffer from a significant disadvantage in that they become brittle when dry and cannot survive more than one or two cycles of hybridization and washing, i.e., "reprobing."

Extensive use today is made of polyamide matrices, in particular nylon matrices, as solid support for immobilization and hybridization of nucleic acids. Various types of nylon are known to bind nucleic acids irreversibly and are far more durable than nitrocellulose. As nucleic acids can be immobilized on nylon in buffers of low ionic strength, transfer of nucleic acids from gels to a nylon matrix can be carried out electrophoretically, which may be performed if transfer of DNA by capillary action or vacuum is inefficient. Two basic types of nylon membranes are commercially available, unmodified nylon and charge-modified nylon. Charge-modified nylon is preferred for transfer and hybridization as its increased positively charged surface has a greater capacity for binding nucleic acids (See, e.g., U.S. Pat. No. 4,473,474, the disclosure of which is herein incorporated in its entirety by reference). Nylon membranes must be treated to immobilize the DNA after it has been transferred, as by way of thorough-drying, or exposure to low amounts of ultraviolet radiation (254 nm).

While polyamide matrices have found considerable use in isotopic assay systems, such matrices have not found widespread use in fluorescent assay systems. This is likely because fluorescent assay systems employing polyamide substrates demonstrate less than desirable sensitivity. Such reduction in sensitivity has been attributed primarily to two factors—background fluorescence produced by the nylon itself, and light scattering by solid materials in contact with the reaction media (such as substrates to which reactants are attached, or walls of the containers in which measurements are made). Polyamides, such as nylon, show light-stimulated endogenous fluorescent emissions and light reflection which can coincide with the range of UV-visible wavelengths emitted from fluorophore-tagged analytes. When light in the excitation waveband causes fluorescence of the support material, interference with detection occurs if the emission waveband of the fluorophore overlaps the same.

While isotopic assays, overall, are very sensitive, they suffer from a number of disadvantages. Primarily, use of any radioisotope automatically invokes health concerns and a host of regulatory duties with respect to waste disposal, safety, handling, reporting and licensing. While present luminescent assays proffer an alternative to isotopic labeling, the sensitivity of such assays is still not within a range desired by many in the biomedical, genetic research and drug discovery communities. Additionally, isotopic labeling cannot be used in multiplex assays, in which two or more nucleic acid probes which have been separately labeled each with their own unique wavelength-emitting luminescent molecule can be simultaneously hybridized, then simultaneously detected on an array of bound nucleic acid targets affixed to the polymeric substrate. Multiplexing saves significant cost and time when compared to the traditional steps of stripping and reprobing when performing multiple queries on a given array of targets. Multiplexing also reduces error and signal degradation that is associated with multiple reprobings.

Thus, there is a need for a relatively thin, multi-cell non-luminescent substrate useful for Micro-Analytical Diagnostic Applications. Such composite microarray non-luminescent slides' structure should be naturally hydrophilic. Such composite microarray non-luminescent slides' properties should be easily controlled. Such composite microarray non-luminescent slides should be more physically robust than the nitrocellulose membrane slides of the prior art. Such composite microarray non-luminescent slides should be relatively easily manufactured. Such composite microarray non-luminescent slides should at least minimize, if not eliminate, any glue/adhesive layer between the membrane and the solid substrate which adds thickness to the membrane/substrate combinations. Such composite microarray non-luminescent slides should have a surface treatment for a substrate that prepares the substrate to operatively, covalently bond to la microporous membrane formed by a phase inversion process such that the combination produced thereby is useful in microarray applications. Such composite microarray non-luminescent slides should include a surface treatment that has no discernable finite thickness or mass which could add nonuniformity to the overall thickness of the composite microarray slides having a porous membrane formed by a phase inversion process useful in microarray applications. Such composite microarray non-luminescent slides should include a surface treatment that at least minimizes, if not eliminates, the participation of this treatment in the binding or detection of nucleic acid or protein analytes by a composite microarray slides having a porous membrane formed by a phase inversion process useful in microarray applications. Such composite microarray non-luminescent slides should include a porous membrane formed by a phase inversion process useful in microarray applications which includes a surface treatment to the solid substrate that minimizes the interference of the substances used to connect the solid substrate portion to the porous membrane portion used for the detection of analytes. Such composite microarray cell non-luminescent slides should include a porous membrane formed by a phase inversion process useful in microarray applications which includes a surface treatment that eliminates nonuniformity of the overall thickness of the substrate/membrane combination structure which is associated with using a third component having a finite thickness or mass as the connecting agent. Such composite microarray non-luminescent slides should have a regular surface on the micro scale. Such composite microarray non-luminescent slides should eliminate compatibility issues between the glue/adhesive and the analyte. Such composite microarray slides should be economically produced. Such composite microarray non-luminescent slides should be for use in luminescent assays which lead to greater sensitivity for detecting analytes in a sample. Such composite microarray slides should allow for simultaneous use of different fluorescently labeled tags for simultaneous detection of multiple analyte molecules.

SUMMARY OF THE DISCLOSURE

An object of the present disclosure is to provide composite microarray non-luminescent slides having a surface treatment for a substrate that prepares the substrate to operatively, covalently bond to a microporous membrane formed by a phase inversion process such that the combination produced thereby is useful in microarray applications.

Another object of the present disclosure is to provide a surface treatment that has no discernable finite thickness or mass which could add nonuniformity to the overall thickness of composite microarray non-luminescent slides having a porous membrane formed by a phase inversion process useful in microarray applications.

A further object of the present disclosure is to provide a surface treatment that minimizes participation in the binding or detection of nucleic acid or protein analytes of composite microarray non-luminescent slides having a porous membrane formed by a phase inversion process useful in microarray applications.

Yet a further object of the present disclosure is to provide composite microarray non-luminescent slides having a porous membrane formed by a phase inversion process useful in microarray applications which includes a surface treatment that minimizes the interference of the substances used to connect the solid substrate portion to the porous membrane portion thereof with the detection of analytes.

Yet another object of the present disclosure is to provide a method for fabricating composite microarray non-luminescent slides having a surface treatment for a substrate that prepares the substrate to sufficiently, covalently bond to a microporous membrane formed by a phase inversion process such that the combination produced thereby is useful in microarray applications.

Still another object of the present disclosure is to provide composite microarray non-luminescent slides having a porous membrane formed by a phase inversion process useful in microarray applications which includes a surface treatment that eliminates nonuniformity of the overall thickness of the substrate/membrane combination structure which is associated with using a third component having a finite thickness or mass as the connecting agent.

In accordance with these and further objects, one aspect of the present disclosure includes a method of fabricating non-luminescent composite microarray slides useful for carrying a microarray of biological polymers comprising the acts of: providing a non-porous substrate; providing a non-luminescent microporous membrane formed by a phase inversion process, the process comprising the acts of: formulating a dope comprising a solvent, one or more non-solvents, opaque solids, and polyamide(s); mixing the dope to cause dissolution of the polyamide and opaque solids therein; producing an opaque solids-filled phase inversion dope; casting a portion of the opaque solids-filled phase inversion dope; and quenching the cast portion of the opaque solids-filled phase inversion dope to form a non-luminescent, microporous membrane; providing a surface treatment; applying the surface treatment to the non-porous substrate; and intermingling the non-porous substrate having the surface treatment with the non-luminescent, microporous membrane such that the non-porous substrate is sufficiently covalently bonded to the non-luminescent microporous membrane wherein the combination produced thereby is useful in microarray applications.

Another aspect of the present disclosure includes composite microarray slides useful for carrying a microarray of biological polymers comprising: a substantially non-reflective microporous membrane which provides little fluorescence from about three hundred (300) nm to about seven hundred (700) nm formed by a phase inversion process, the non-reflective microporous membrane comprising: a phase-inversion support; and a plurality of opaque solids that are substantially chemically non-reactive with the phase inversion support and intimately bound to, and/or partially/completely contained within, said phase-inversion; a non-porous substrate; and a surface treatment, operatively positioned between the substantially non-reflective microporous membrane and the non-porous substrate, for sufficiently covalently bonding the non-porous substrate to the microporous membrane wherein the combination composite microarray slides produced thereby are useful in microarray applications.

A third aspect of the present disclosure includes composite microarray slides useful for carrying a microarray of biological polymers comprising: an optically passive substrate comprising: a phase-inversion support and opaque solids that are substantially non-reactive chemically with the phase-inversion support, in a weight ratio with the phase-inversion support such that they optically passive substrate absorbs light at substantially all wave lengths from about three hundred (300) nm to about seven hundred (700) nm; a non-porous substrate; and a surface treatment, operatively positioned between the optically passive substrate and the non-porous substrate, for sufficiently covalently bonding the non-porous substrate to the optically passive substrate wherein the, combination microarray slides produced thereby are useful in microarray applications.

Another aspect of the present disclosure may include a post-treatment of the non-luminescent microporous membrane such that the membrane contains a greater positive charge; such a treatment is useful in augmenting the microporous membrane's ability to retain biological polymers, which predominantly are negatively charged.

Other objects and advantages of the disclosure will be apparent from the following description, the accompanying drawings and the appended claims.

BRIEF DESCRIPTION OF THE DRAWINGS

FIG. 1 is a graphic depiction of representative organosilanes useful with the present application;

FIG. 2 is a representative graphic depiction of the hydrolysis of an organosilane to produce an organosilanol useful with the present application;

FIG. 4A is a representative graphic depiction of a reaction of an epoxy with an amino functional group useful with the present application;

FIG. 4B is a representative graphic depiction of a reaction of an epoxy with an carboxyl functional group useful with the present application;

DETAILED DESCRIPTION OF REPRESENTATIVE EMBODIMENTS

Figure 3:
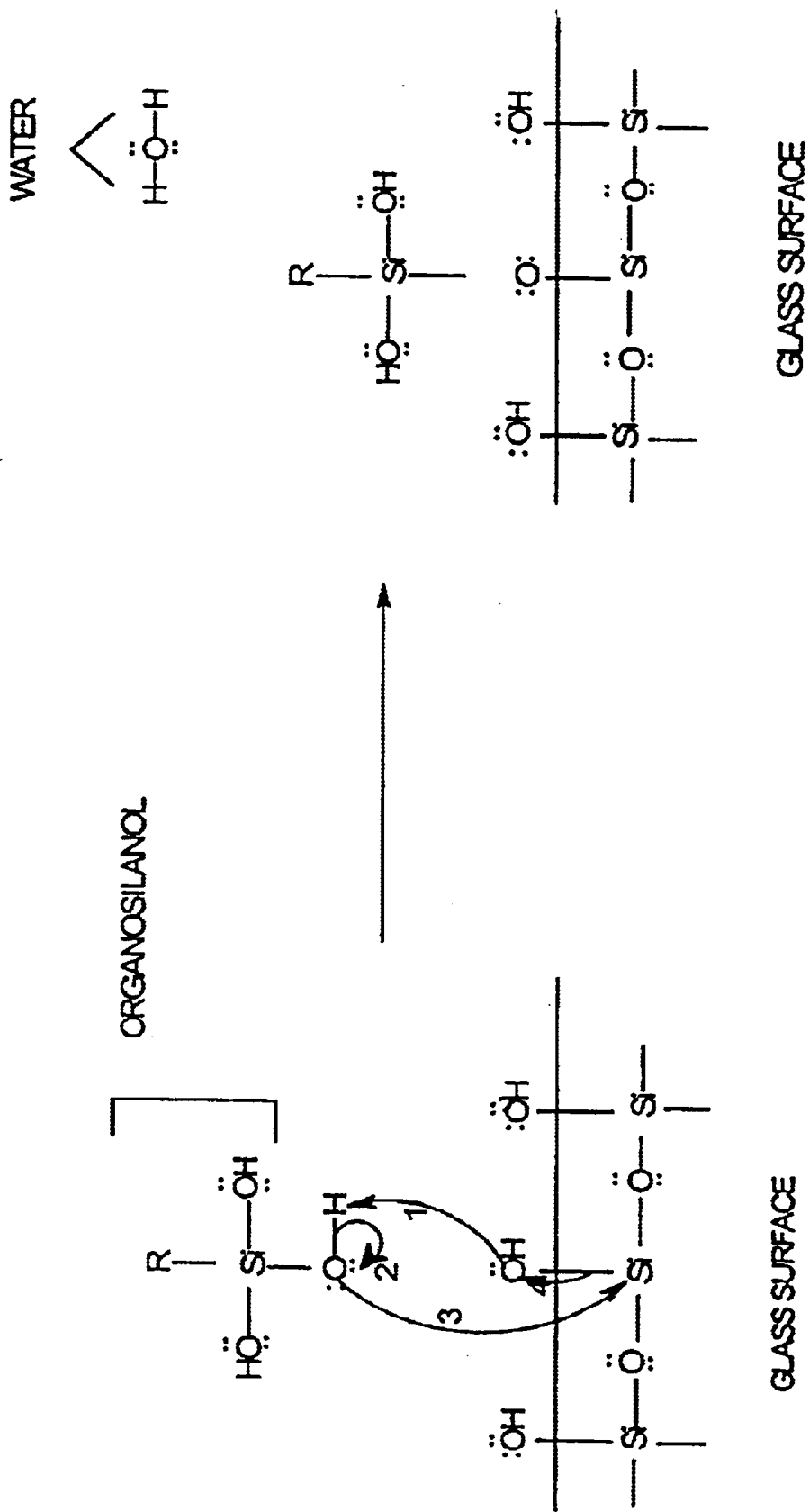
FIG. 3 is a representative graphic depiction of a silanol condensation reaction in which the silanol in solution condenses with the silanol on the glass surface, expelling water and creating the treated glass surface of the present application.

Unless indicated otherwise, the terms defined below have the following meanings:

"Analyte" or "analyte molecule" refers to a molecule, typically a macromolecule, such as a polynucleotide or polypeptide, whose presence, amount, and/or identity are to be determined. The analyte is one member of a ligand/anti-ligand pair.

"Analyte-specific assay reagent" refers to a molecule effective to bind specifically to an analyte molecule. The reagent is the opposite member of a ligand/anti-ligand binding pair.

An "array of regions on a solid support" is a linear, two-dimensional array or 3-D arrays of preferably discrete regions, each having a finite area, formed on the surface of a solid support.

A "microarray" is an array of regions having a density of discrete regions of at least about 100/cm$^2$, and preferably at least about 1000/cm$^2$. The regions in a microarray have typical dimensions, e.g., diameters, in the range of between about 10–250 µm, and are separated from other regions in the array by about the same distance.

A "phase inversion process" is meant to encompass the known art of porous membrane production techniques which involve phase inversion in its various forms, to produce "phase inversion membranes" By "phase inversion membranes" it is meant a porous membrane that is formed by the gelation or precipitation of a polymer membrane structure from a "phase inversion casting dope." A "phase inversion casting dope" consists of a continuous phase of dissolved polymer in a good solvent, co-existing with a discrete phase of one or more non-solvents dispersed within the continuous phase. In accordance with generally acknowledged industry practice, the formation of the polymer membrane structure generally includes the steps of casting and quenching a thin layer of the dope under controlled conditions to affect precipitation of the polymer and transition of discrete (non-solvent phase) into a continuous interconnected pore structure. In one manner of explanation, this transition from discrete phase of non-solvent (sometimes referred to as a "pore former") into a continuum of interconnected pores is generally known as "phase inversion." Such membranes are well known in the art. Occasionally, such membranes and processes will be called "ternary phase inversion" membranes and processes, with specific reference to the ability to describe the composition of the casting dope in terms of the three major components; polymer, solvent, and non-solvent (s). The presence of the three major components comprise the "ternary" system. Variations of this system include: liquid phase inversions evaporative phase inversion, thermal phase inversion (where dissolution is achieved and sustained at elevated temperature before casting and quenching), and others.

Composite microarray slides comprise a porous nylon or other polymer membrane bound to a solid, backing, typically a glass microscope slide. Microarray slides are used in gene sequencing and expression analysis applications where thousands, of hybridization assays are performed simultaneously on the surface of a single microarray slide.

When a microporous nylon membrane formed by phase inversion process is still wet from casting, the nylon membrane has a greater thickness than after being dried. If the membrane is stretched out over a surface and then dried, the nylon membrane shrinks in the direction of thickness. The nylon membrane also binds tightly to the surface it contacts. If the nylon membrane has been dried once and then rewetted, the nylon membrane does not exhibit the binding property described above. More importantly, the nylon membrane loses the binding property once the nylon membrane is wetted after having been tightly bound to a surface.

Given the above characteristic of nylon membrane, it was decided to attempt to find mechanisms for attachment of nylon membrane to a substrate, such as, for example, glass, such that the bond between the nylon membrane and the substrate would remain intact after being exposed to various known severe conditions experienced in actual practice. For example, the nylon/solid composite slide should withstand immersion in an about eighty degrees Celsius (80° C.), about one percent (1%) sodium dodecyl sulfate (SDS) solution. For the purposes of the present application, an organosilane has the formula:

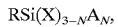

$$RSi(X)_{3-N}A_N,$$

where X is an ethoxy, methoxy, or chloride group, and R is a functional group that interacts with nylon, or with an intermediate substance capable of bonding to nylon. The 'A' group is an additional unreactive group that may or may not be present (depending on whether N is 0, 1, or 2). In the case of nylon, as examples, R could contain ureido, amino, carboxy, epoxy or other functional groups capable of bonding directly to nylon or to some intermediate substance that is capable of bonding to nylon.

Based on various experiments, some organosilane treatments appeared to be very feasible to bind porous nylon membrane to glass in a way that does not affect the chemical or physical properties of the membrane.

An effective method for bonding the nylon to the solid substrate has been developed. In this method, glass slides were first immersed in a 2% solution of 3-aminopropyl triethoxysilane (an aminosilane) in aqueous ethanol for two minutes. After the treated slides were cured for about a day at room temperature, the slides were immersed in an about 3.5% solids solution of a polyamido-polyamine epichlorohydrin resin (specifically 'Resicart E', manufactured by Ciba-Geigy) containing tetraethylene pentamine (TEPA) for about one hour. The slides were then rinsed with DI water, laminated with the membrane, and further cured in an oven at about one hundred twenty degrees Celsius (120° C.) for about one hour. The newly prepared composites were then cured at room temperature for at least a day before being tested. This method was designated Aminosilane-Resicart-Coat (ARC).

Though Resicart E is inherently positively charged, the functional surfaces of the composites do not show properties of the positive charge of Resicart E. This is because the Resicart E is only present at the interface between the nylon and the glass, and not present as a coating on the internal or external surfaces of the nylon membrane, that is, Resicart E is not functioning as a surface charge modifier to nylon.

To charge modify the ARC composites, a separate charge modification step is required. For example, the cured samples were immersed in about a 3.5% solids Resicart E with TEPA for about 3 minutes, rinsed well with DI water, shaken to remove excess water (eliminating the gloss of water from the surface), and heated in an oven at about sixty degrees Celsius (60° C.) until dry. Other methods of charge-modifying the nylon portion of the membrane are possible, for example, a spray, brush, or foam application of charge modifier on the upper surface of the membrane. Alternatively, a pre-modified layer of nylon microporous membrane can be produced by direct addition of charge modifying chemistry to the nylon casting dope.

Incubation of membrane-glass composite slide in a 1.0% SDS solution at about 80° C., did not separate the uncharged ARC samples from the substrate. The cosmetic appearance and bond strength of the above mentioned unmodified slides after immersion were generally good. The bond strength was stronger than the membrane's tensile strength even after the composite was subjected to near-boiling 1% SDS for about one hour.

The aforementioned charge modified ARC-samples also remained bonded, but the bond strength tended to be weaker than the unmodified slides. The longer the charge modified ARC composites cured (at room temperature) before being tested, the stronger the bond. Results indicate that if they were tested a day after being charge treated, they had only fair bond strength after SDS exposure. If allowed to cure for a week or more, the composites' bond strength tended to be very good. When submerged in dilute solution of metanil yellow dye (a negatively charged compound), the charged ARC samples showed uniform binding of the dye on the surface, indicating even positive charge distribution. The interface layer of the composites (charged and uncharged) showed a high binding of dye too—indicating that Resicart E is present at the interface (as expected). Therefore, all surfaces (internal and external) of the full thickness of the nylon structure have been charge modified. It should be possible to restrict the charge modification to the upper surface by a different application technique, as mentioned above.

While not wishing to be bound by theory, it is presently believed that the following describes the chemistry controlling the bonding of the nylon to the glass in the nylon/glass composite slides described above and in the Examples.

As illustrated in FIG. 1, in the first step of bonding the nylon to the glass substrate about 2 mL of an organosilane is mixed into a solution containing about 95 mL ethanol and about 5 mL water. As shown, the representative organosilane contains four functional groups.

Concerning the present application, the chemistry of the single 'R' functional group is of particular interest. Of the remaining three functional groups on the organosilane, at least one is a hydrolyzable 'X' group. In the present application, the representative organosilane may or may not contain functional groups of other types than the 'R' functional group (which will be defined) and the 'X' functional group (which is an ethoxy-, a methoxy-, or a chloride, any of which is sufficient for the purposes of the present application). If the organosilane does contain other kinds of functionalities (most often a hydrogen or an alkyl group), they are non-reactive and are represented by an 'A' in the drawings.

As illustrated by the reaction depicted in FIG. 2, the water in the solution with the organosilane hydrolyzes the X functional groups and produces an organosilanol. This reactive process takes at most about five minutes.

As shown in FIG. 3, once the organosilanol is formed, the solution reacts with glass. As illustrated, the organosilanol bonds to the glass surface, giving the glass the surface chemistry of the 'R' functional group.

If the 'R' is an amino or a carboxyl functional group, the glass slide is then exposed to about a 3.54 solids solution of a polyamido-polyamine epichlorohydrin resin. In this reaction, an epoxy group on the resin polymer bonds with an amino functional group or a carboxyl functional group according to the illustrations in FIGS. 4a and 4b, respectively.

The other end of the polyamido-polyamine epichlorohydrin polymer has another epoxy functional group capable of bonding to amino or carboxyl functional groups present in nylon.

At this point in the process, the wet-as-cast nylon membrane is placed on top of the wetted, treated glass slides, stretched and clipped into place. After drying for about one hour at about one hundred twenty degrees Celsius (120° C.), the membrane dries thereby bonding to the glass surface and the epoxy functional groups of the epichlorohydrin polymer bond to amino or carboxyl functional groups on the nylon.

This reaction proceeds as illustrated in FIG. 4a and FIG. 4B, according to whether the group is an amino functional group or a carboxyl functional group, respectively.

If the 'R' functional group of the organosilanol initially contains an epoxy functional group, the 'R' functional group of the organosilanol can bond directly with the nylon without exposure to polyamido-polyamine epichlorohydrin polymer. As before, the epoxy group bonds to either amino functional groups or to carboxyl functional groups on the nylon, as illustrated in FIGS. 4A–B. The nylon membrane is stretched over the membrane and clipped and dried as described above.

Figure 5A:
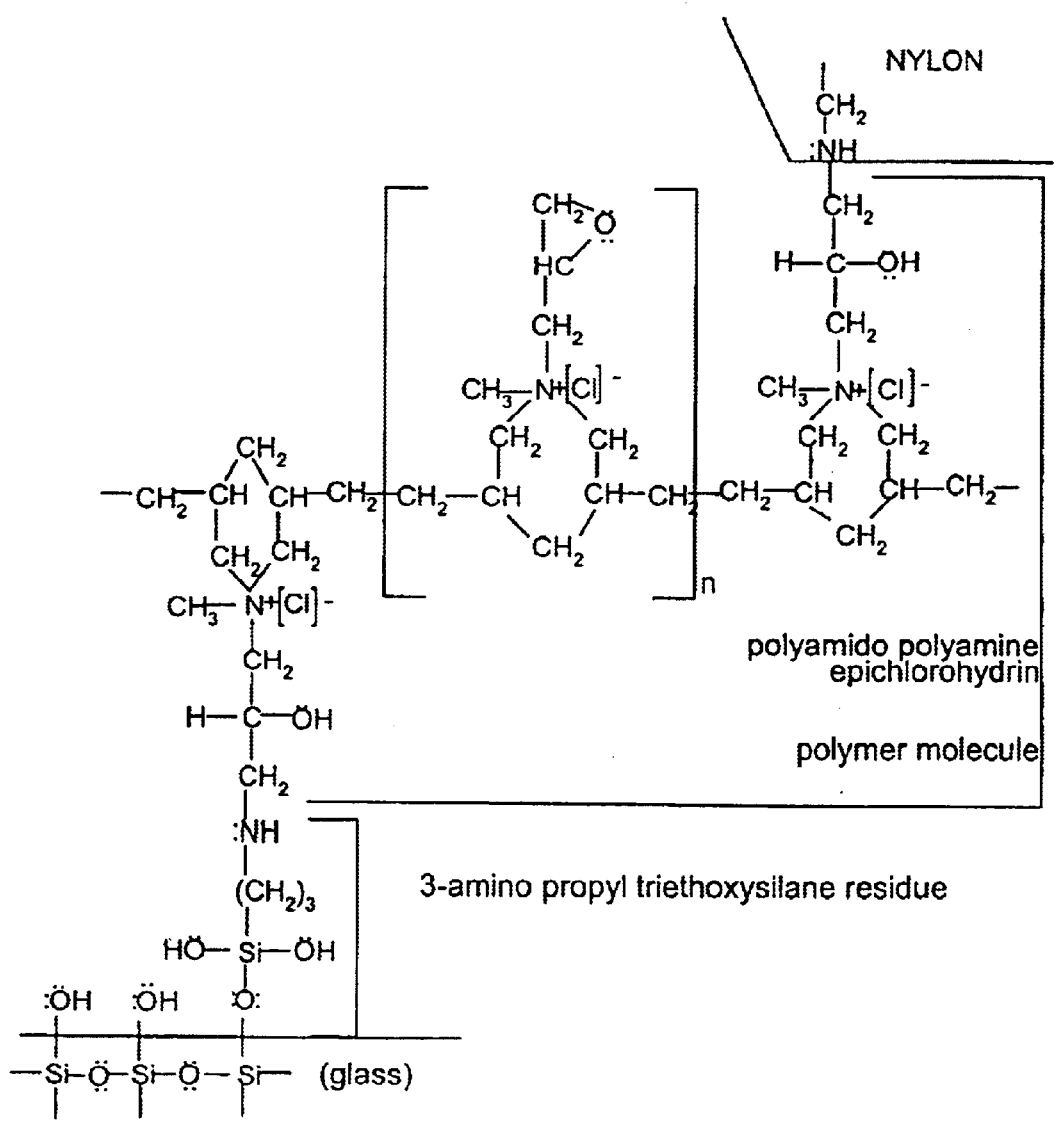
FIG. 5A is a representative graphic depiction of a bond between nylon and glass resulting from using 3-aminopropyl triethoxysilane and polyamido-polyamine epichlorohydrin polymer useful with the present application.
Figure 5B:
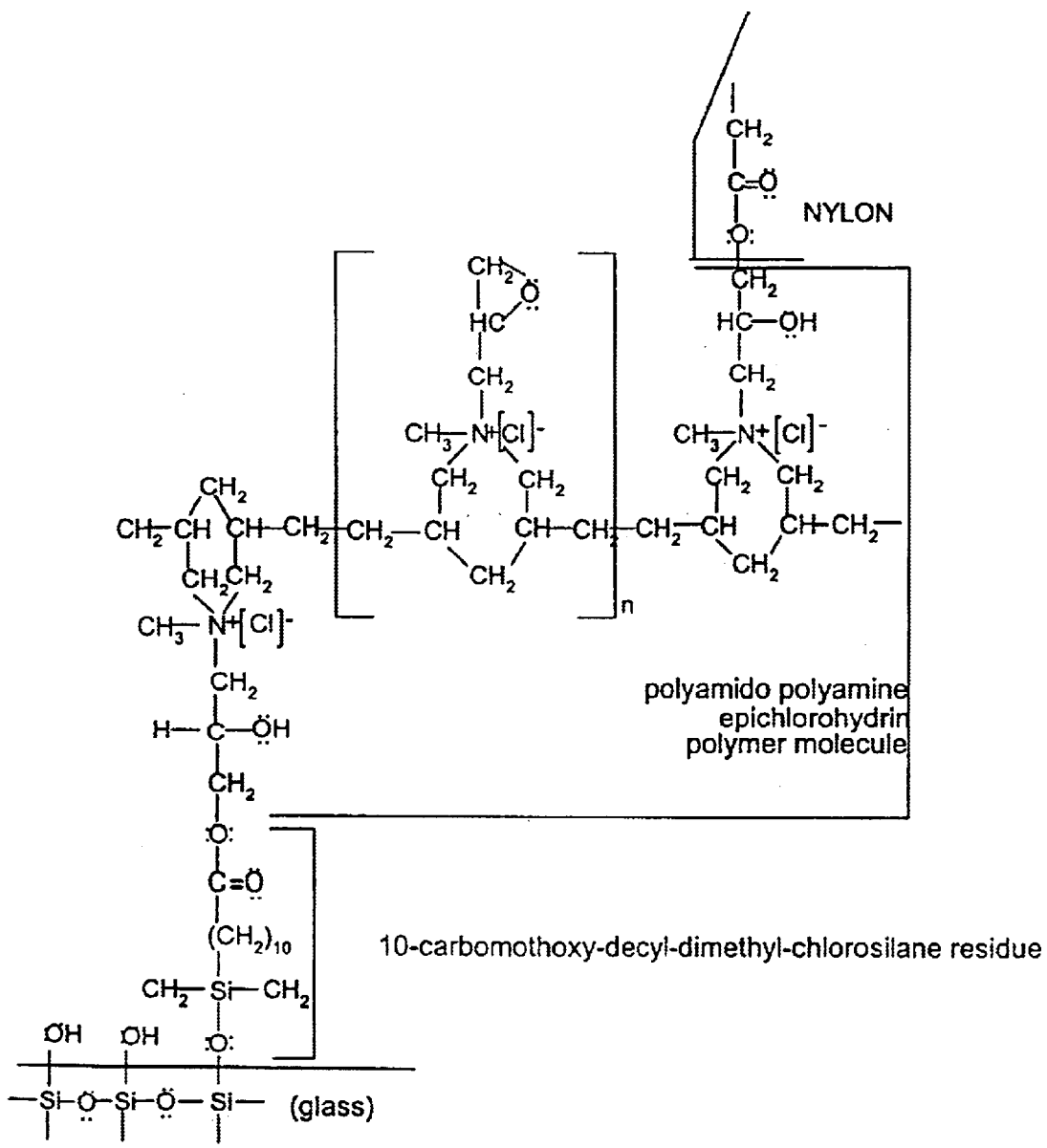
FIG. 5B is a representative graphic depiction of a bond between nylon and glass resulting from using 1-carbomethoxy-decyl-dimethyl chlorosilane and polyamido-polyamine epichlorohydrin polymer useful with the present application.
Figure 5C:
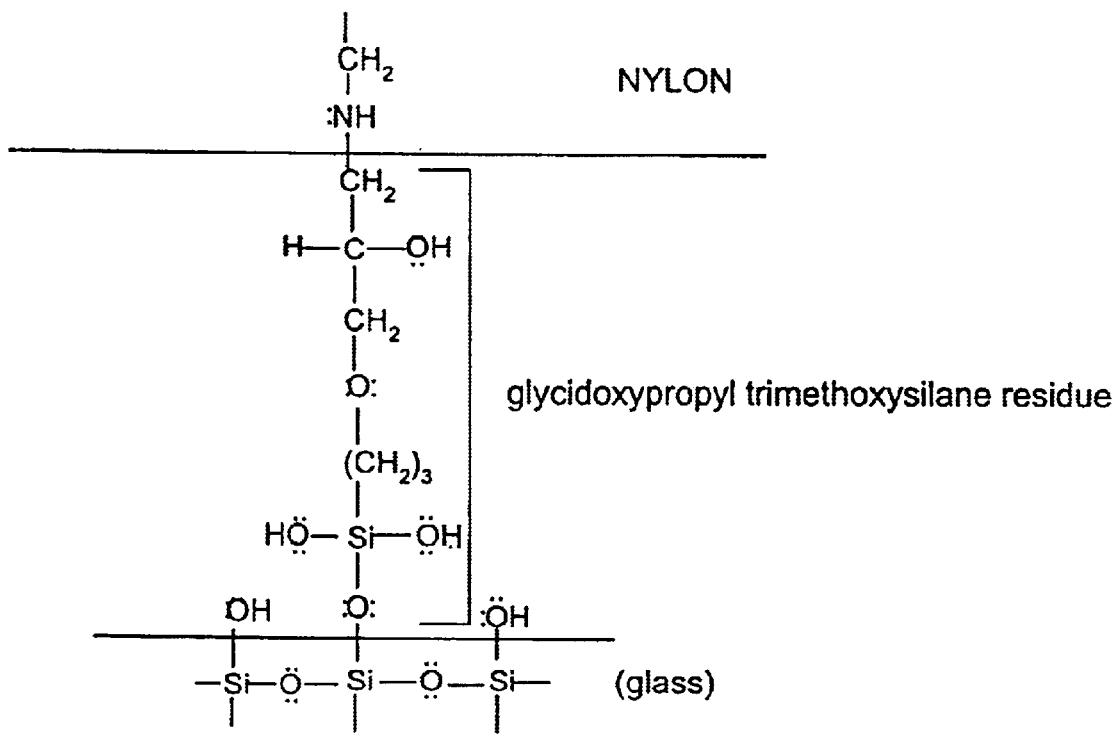
FIG. 5C is a representative graphic depiction of a bond between nylon and glass resulting from using glycidoxypropyltrimethoxysilane useful with the present application.

FIGS. 5A–C illustrates the final chemical structure of the nylon/glass composite slide depending on the particular kind of functional group the 'R' group represents. FIG. 5A illustrates a nylon/glass composite slide in which the 'R' group ends in an amino functional group (specifically, the silane is 3-aminopropyl triethoxysilane). FIG. 5B illustrates a nylon/glass composite slide in which the 'R' group ends in a carboxyl functional group (specifically 10-carbomethoxy-decyl-dimethyl chlorosilane). In FIGS. 5A and 5B, note that the polyamido-polyamine epichlorohydrin polymer molecule forms a bridge between the organosilane end group and the nylon.

FIG. 5C illustrates a composite in which the 'R' group is an epoxy functional group (specifically glycidoxypropyl trimethoxysilane). Notice that there is no polymer molecule bridging between the organosilane end group and the nylon group.

From an analysis of the nylon/glass composite slides made in accordance with the following examples, a significant portion of the glass and the nylon are in direct contact, thereby avoiding a complete separate layer of material between the two slide components. In this manner, the bonding of nylon to glass has been accomplished without the use of an adhesive or gluing layer having any appreciable thickness.

The general procedure for producing multi cell composite microarray slides useful for carrying a microarray of biological polymers on the surface thereof and specifically nylon composite microarray slide operatively connected to a glass slide is described below.

Figure 6:
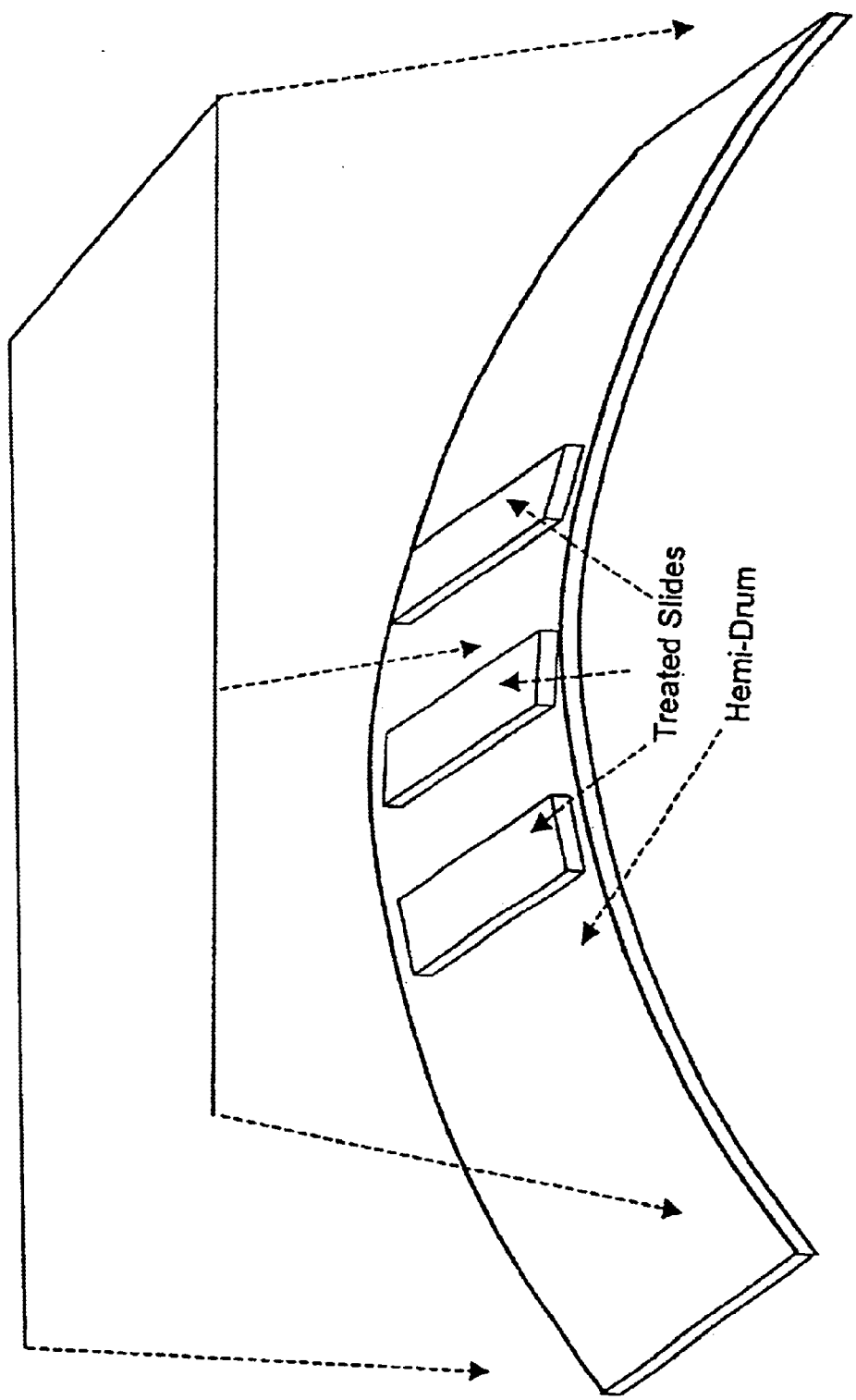
FIG. 6A is a graphic depiction of three slides on a metal hemi-drum.
FIG. 6B shows a graphic representation of the wetted, treated slides on the hemi-drum.
FIG. 6C is a representative graphic description of the wet-as-cast-nylon membrane stretched and positioned over the treated slides.
FIG. 6D is a representative graphic description of the wet-as-cast-nylon membrane secured into position.
Figure 6A:
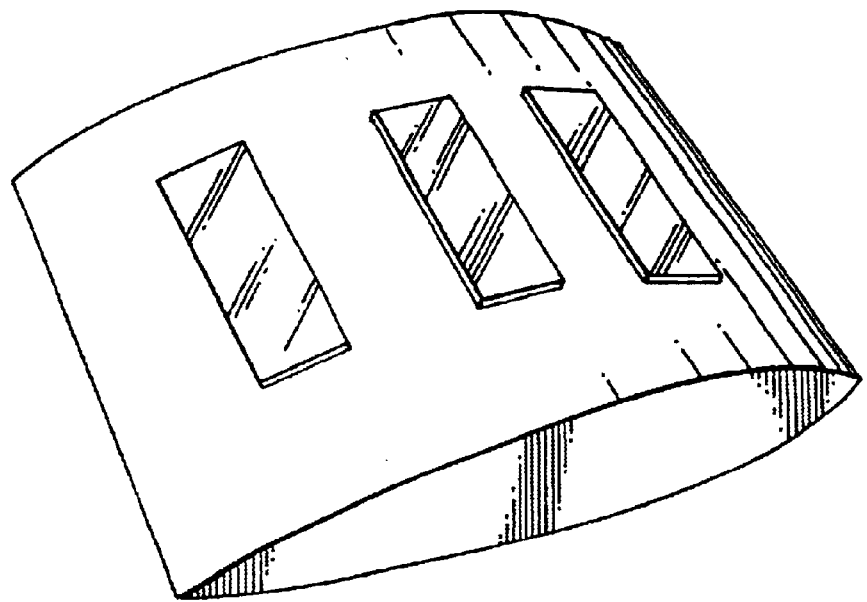
Figure 6B:
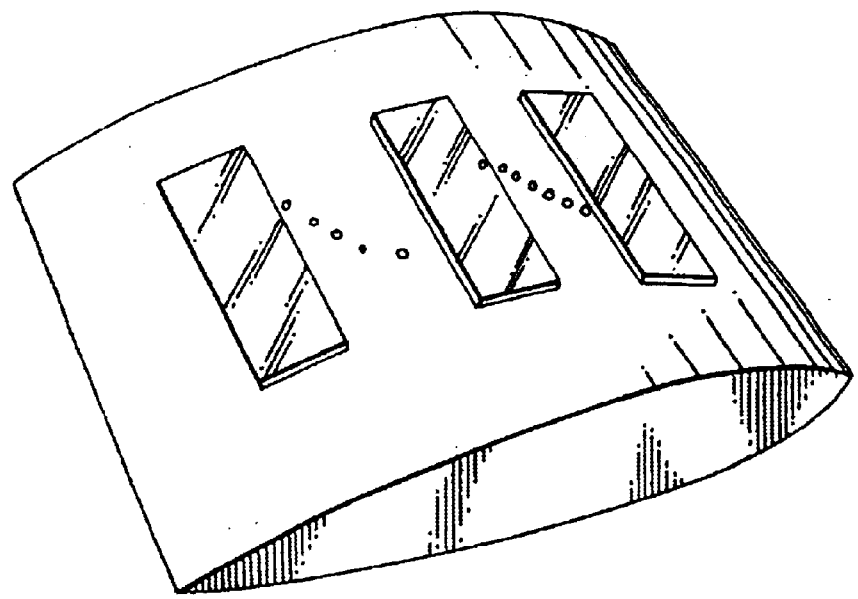
Figure 6D:
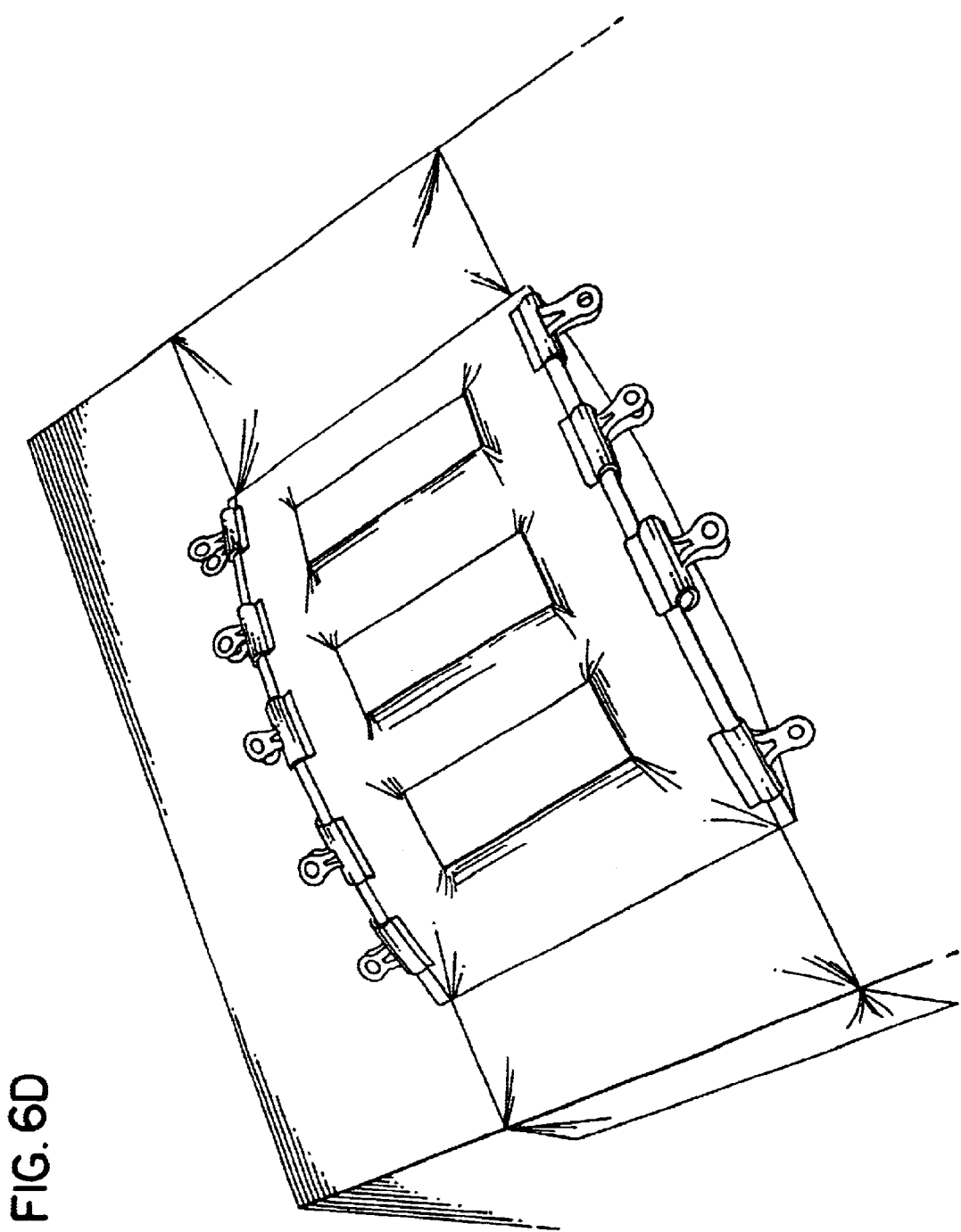
Figure 7:
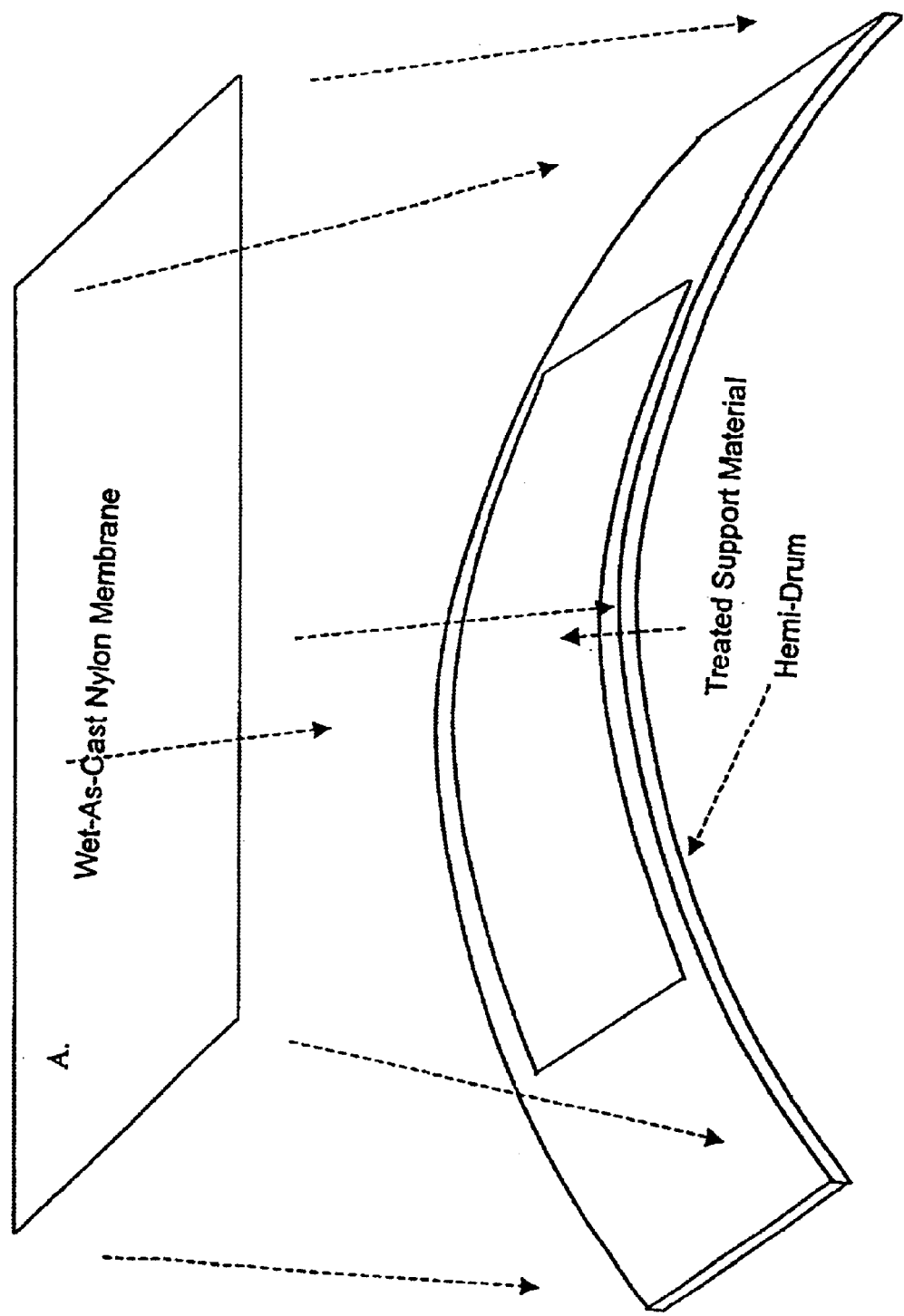
FIG. 7A is a Graphic description of a Mylar sheet material placed on a metal hemi-drum.
FIG. 7B shows a representative graphic description of the wetted, treated Mylar sheet on the hemi-drum.
FIG. 7C is a representative graphic description of the wet-as-cast-nylon membrane stretched and positioned over the treated Mylar sheet material.
FIG. 7D is a representative graphic description of the wet-as-cast-nylon membrane secured into position.
Figure 7A:
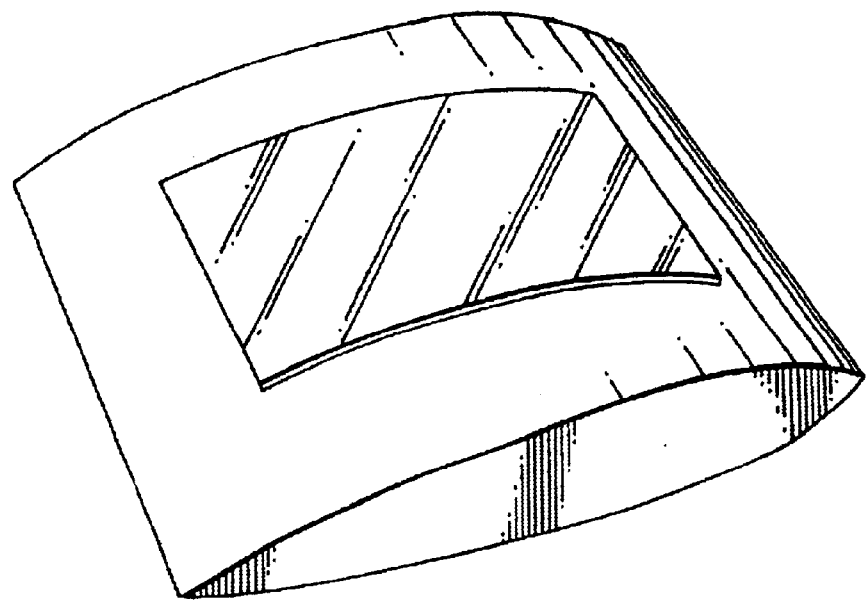
Figure 7B:
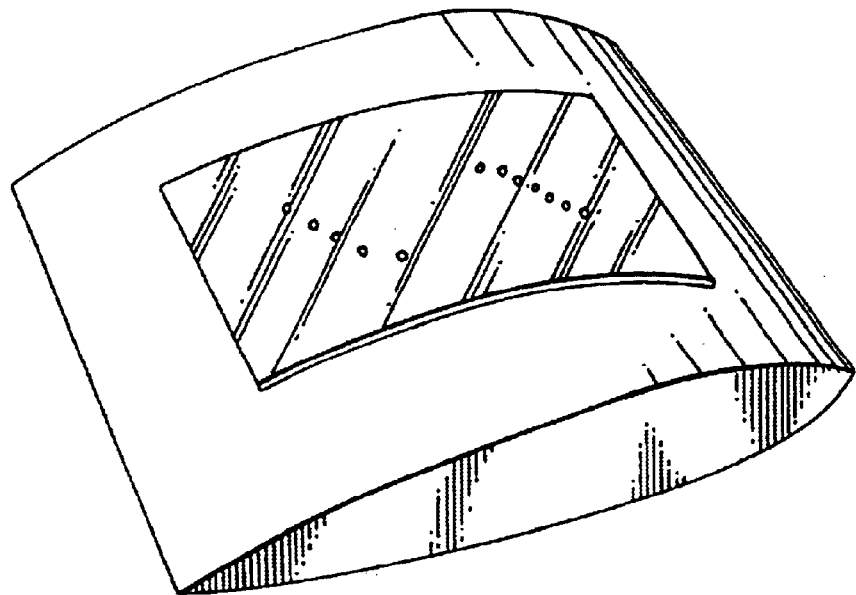
Figure 7C:
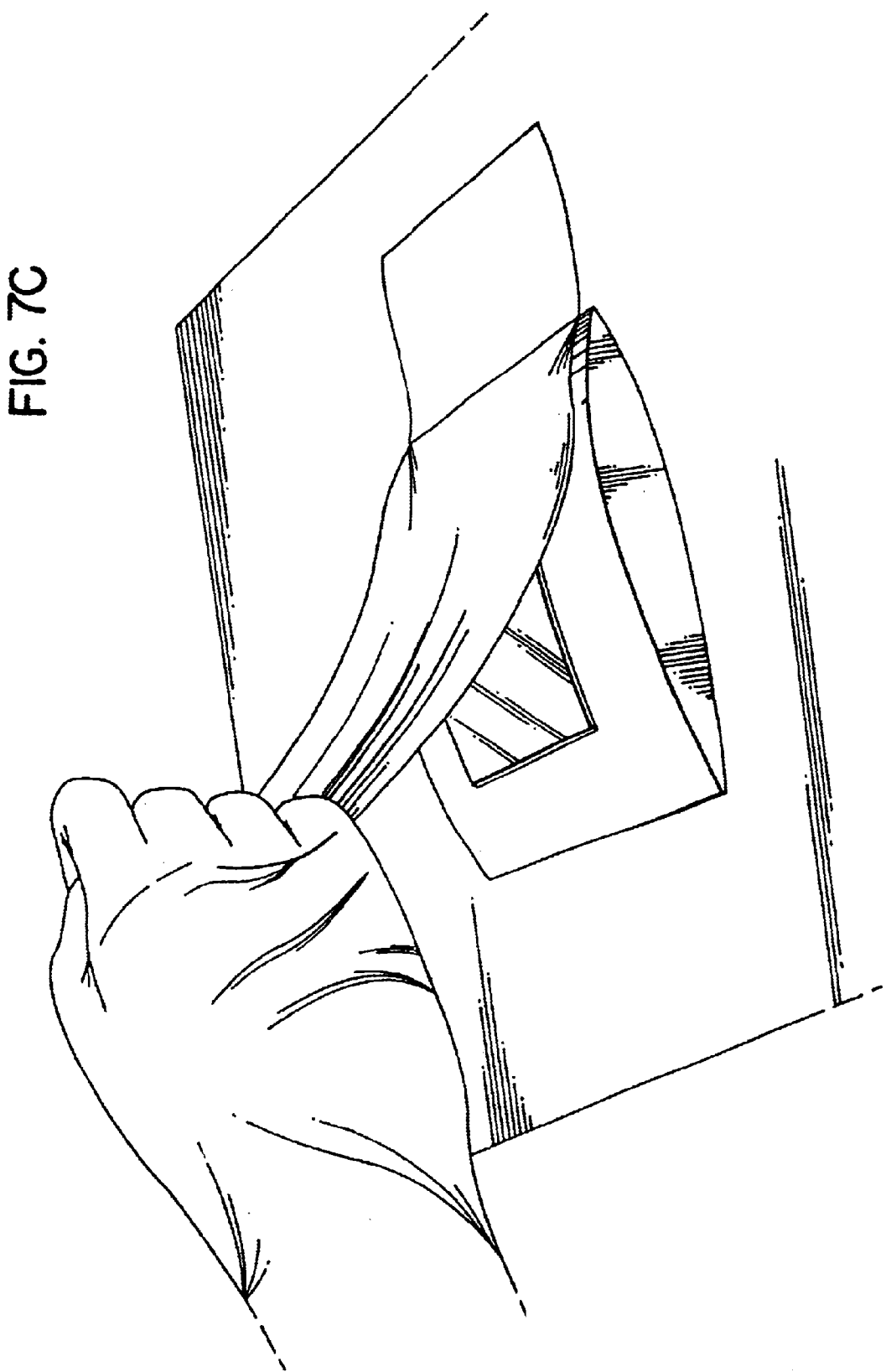
Figure 7D:
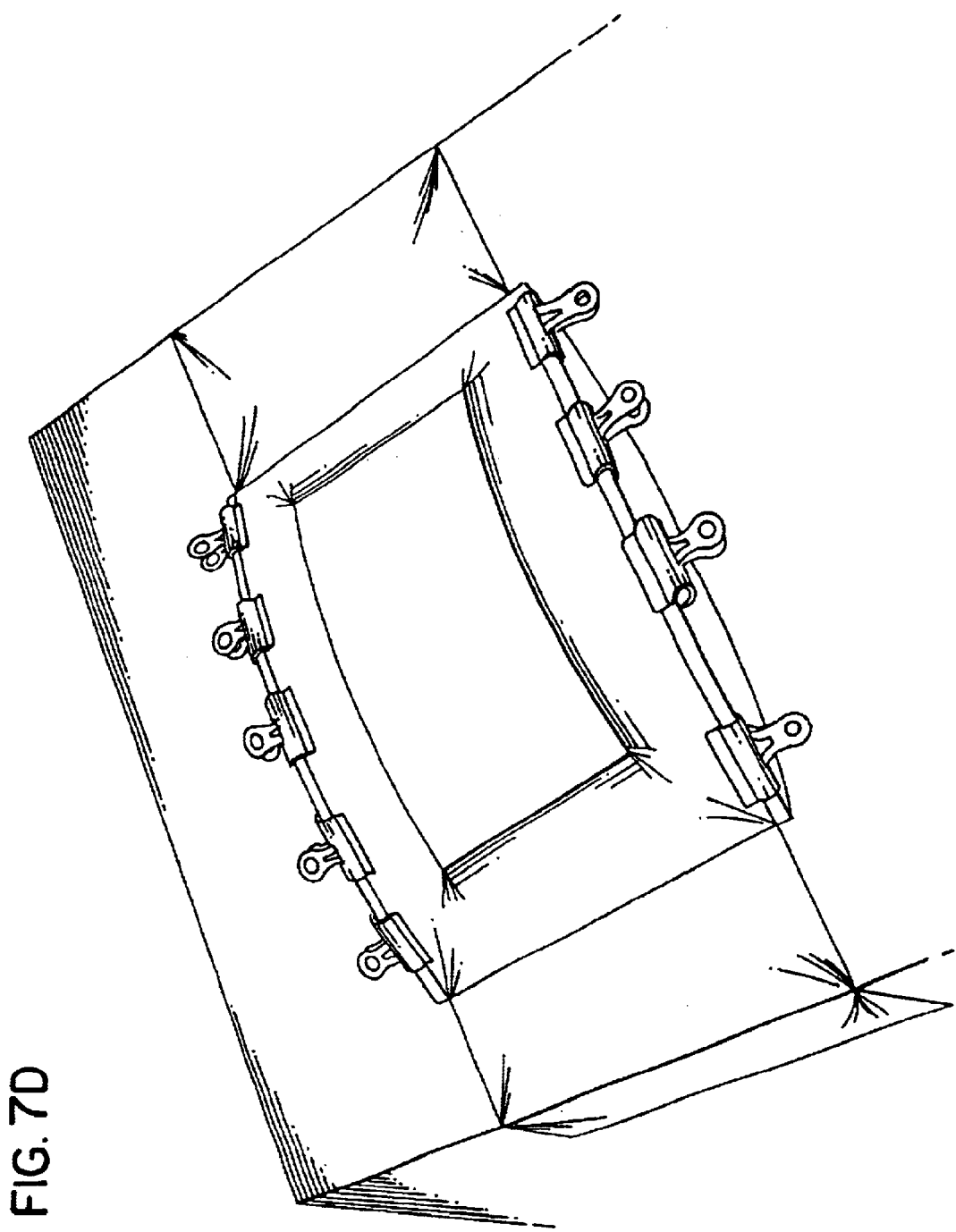

A metal hemi-drum, useful in the production of such slides, is illustrated in FIGS. 6A–D and 7A–D. It is advantageous to use a metal drum having an outside surface which has been pre-coated with a permanent Teflon coating (such as in non-stick skillets). Using the metal hemi-drum of FIGS. 6 and 7, the slides treated as described above are placed thereon. Next, the surface that will interface with the wet-as-cast-nylon membrane of each treated slide is covered with DI water. (Please see FIGS. 6A–B and 7A–B for representative examples.) An amount of the wet-as-cast-nylon membrane sufficient to cover each treated slide is stretched and positioned over the treated slides, making sure that there are no air bubbles between the glass and the wet-as-cast-nylon membrane. (FIGS. 6C and 7C for representative examples.) Once the wet-as-cast-nylon membrane is positioned over the treated slides, the wet-as-cast-nylon membrane is secured in position using conventional devices, such as, for example, clips (e.g., as shown in FIGS. 6D and 7D).

The wet-as-cast-nylon membrane/glass slide combinations were placed in a convection oven for a period of about one hour at about one hundred twenty degrees Celsius (120°) C. Upon completion of the drying process, the glass to membrane bond has been formed, and the attachment is strong. The combined sheet of membrane plus glass slides is easily peeled off of the teflon coated metal drum, and then the excess nylon membrane is trimmed from the glass slides, with any suitable trimming technique (razor cut, die cut, shear cut, etc.) as is known in the art.

The above methodologies were directed to regular non-treated multi-cell non-luminescent substrate useful for carrying a microarray of biological polymers on the surface thereof However, the present disclosure overcomes many of the problems associated with the less than desirable solid substrates used in analyte assays employing fluorescent labeling, and provides a product useful in a number of other applications, including filtration.

As disclosed in the provisional application incorporated by reference herein directed to non-luminescent substrates, a phase-inversion substrate, impregnated (fully or partially), coated, or surface-bound (or combination of the same), with opaque solids that are non-reactive with the phase inversion support and of a size sufficient to be partially or completely within, or irreversibly bound, to the phase inversion support have at least reduced, if not eliminated the problems of the prior art associated therewith. In a preferred embodiment of that application, the substrate is a membrane, which may or may not carry charge. When employed in analyte assays which are based on luminescent labeling, substrates containing such opaque solids have been found to allow significantly enhanced detection of numerous analytes under many conditions. Such substrates have been seen to produce significantly less intrinsic fluorescence and light-scattering than polyamide substrates lacking the opaque solids.

The term "phase inversion support" was defined in the Andreoli application as a polymeric support that was formed by the gelation or precipitation of a polymer membrane structure from a "phase inversion casting dope." A "phase inversion casting dope," as defined in the Andreoli application consisted of a continuous phase of dissolved polymer in a good solvent, co-existing with a discrete phase of one or more non-solvent(s) dispersed within the continuous phase. The formation of the polymer membrane structure generally included the steps of casting and quenching a thin layer of the dope under controlled conditions to affect precipitation of the polymer and transition of discrete (non-solvent phase) into a continuous interconnected pore structure. This transition from discrete phase of non-solvent (sometimes referred to as a "pore former") into a continuum of interconnected pores is generally known as "phase inversion." Such membranes are well known in the art.

Typically, a phase inversion support is formed by dissolving the polymer(s) of choice in a mixture of miscible solvent(s) and non-solvent(s), casting a support pre-form, and then placing the surface of the support pre-form in contact with a non-solvent (liquid or atmosphere) diluent miscible with the solvent(s) (thereby precipitating or gelling the porous structure).

The term "opaque" was defined in the Andreoli application as displaying the property of not being pervious to visible light. The term "solid" was defined as a composition of matter that is not entirely either a liquid or gas, or both. A "solid" may, or may not, have internal cavities or channels. A "solid" with an internal cavity or channel may comprise a liquid or gas within the internal cavity or channel.

The term "intimately bound" was defined in the Andreoli application as one substance is bound to another substance in a manner that it is not easily dissociated from the other substance. As used in the Andreoli application and this application "intimately bound" does not include binding which is predominantly by means of a chemical bond between the one substance and the other substance.

A preferred phase inversion support disclosed in the Andreoli application comprised polyamides, organic polymers formed by the formation of amide bonds between monomers of one or more types. Particularly useful polyamides in the Andreoli disclosure were nylons. Nylons comprise aliphatic carbon chains, usually alkylene groups, between amide groups. The amide groups in nylons are very polar and clan hydrogen bond with each other, and are essentially planar due to the partial double-bond character of the C—N bond. Nylons are polymers of intermediate crystallinity, crystallinity being due to the ability of the NH group to form strong hydrogen bonds with the C=O group. Nylon typically consists of crystalilites of different size and perfection. It is the amorphous content of nylons that adds a diffuse scattering halo. Nylon 66, typically synthesized by reacting adipic acid with hexamethylene diamine, is a particularly preferred nylon for the present disclosure. Nylon 66 will typically contain both fluorescent and phosphorescent species which can not be extracted by conventional extraction techniques. These species are believed to be associated with the presence of α-ketoimide structures formed by thermal oxidation of the molecular backbone of the polymer, and associated with, or originating from, aldol condensation products of cyclic enone dimer and dienone trimer of cyclopentanone; all of which arc present in the polymer as manufactured (See, Allen et al., *Analysis of the Fluorescent and Phosphorescent Species in Nylon-66*, Eur. Polym. J., 21(6), pp. 517–526, 1985).

A carbon-polyamide substrate of the Andreoli disclosure could be produced by coating the surface of, or impregnating, a polyamide support, such as a mesh, with carbon black.

The polyamide, such as Nylon-66, could be produced with carbon black mixed into a casting dope, such casting dopes as described in U.S. Pat. Nos. 3,876,738 and/or U.S. Pat. No. 4,645,602, so as to form a carbon-black filled polyamide microporous membrane substrate.

Polyamide substrates can be formed into planar solid supports, containers and filters. Preferred polyamide substrates are readily wettable by the liquids with which they are to be contacted, and are preferably hydrophilic. Preferred polyamide substrates are also porous. The polyamide substrate may comprise a microporous membrane. The substrate is preferably also skinless, that is, the polymer organization does not change from the exterior surface to the interior surface of the polyamide. Nylon-66 is a preferred polyamide, particularly in the form of a skinless, hydrophilic microporous membrane.

While any opaque solid that is non-reactive with the phase inversion support and of a size sufficient to be partially or completely contained within, or irreversibly bound to the phase inversion support which has the desired fluorescence quenching properties may be used, black solids in particular, such as carbon-black, have been advantageously employed. Carbon-black absorbs energy thereby quenching the fluorescing background produced by a Nylon-66 membrane. The simple chemistry of carbon black, once incorporated into the membrane, has not been found to interfere with nucleic acid binding assays, in particular with DNA binding during Southern Blot transfer.

Alternatively, it is believed that a suitable coating of pigment (by which it is meant a solid that reflects light or certain wavelengths while absorbing light of other wavelengths, without producing appreciable luminescence) either impregnated partially or mostly within the polymer matrix or properly and intimately bound to the surfaces (internal and external surfaces of the porous matrix) of such a microporous membrane may also be employed; especially when it is desirable to have the chemical functionality of the pigment available for interaction with analytes.

The inventor(s) of the "Improved Non-Luminescent Substrate" application discovered that activated carbon-coated polyamide substrates, in particular nylon substrates, and polyamide substrates having activated carbon partially encompassed therein (i.e., having a portion of the activated carbon particles exposed on the surface of the polyamide substrate) have been found to provide enhanced removal of organic contaminants in drinking water as well as particle removal. The increase in removal of organic contaminants from fluids which is evidenced using activated carbon-polyamide substrates, as opposed to nylon alone, or activated carbon alone, may be due to the greater surface proffered when the activated carbon particles are dispersed among the polyamide support.

The present application is directed to the combination of the "Improved Non-Luminescent Substrate" application with the "Improved Combination of Microporous Membrane and Solid Support for Micro-Analytical Diagnostic Applications" applications. This combination is believed best described in the following example which was designed to illustrate, but in no way intended to limit, the present disclosure.

EXAMPLE 1

Preparation of Low Fluorescence Nylon/Glass Composites

The following example describes the casting of a carbon black impregnated nylon membrane, followed by the permanent attachment of the membrane to a glass slide to form a composite. The final composites consist of a twenty five millimeter (25 mm) by seventy five millimeter (75 mm) glass slide laminated with a nominally 0.2 micron pore size microporous carbon black impregnated nylon membrane that is about 2 mils in thickness.

A dope formulation comprising about sixteen percent (16%) by weight Nylon-66 (Monsanto® Vydyne™ 66Z), about seventy-seven percent (77%) by weight formic acid, and about seven percent (7%) by weight methanol, was produced using the methods disclosed in U.S. Pat. Nos. 3,876,738 and 4,645,602, the disclosure of each is herein incorporated in their entirety by reference. This is the standard formulation and method used to produce the (white) control membrane.

To produce the carbon black-containing membranes of the present example, the method is similar, but altered by adding the carbon black prior to the addition of nylon to the solvent. Specific final compositions for the dopes produced in this example, expressed in % by weight for each component are shown in Table 1A.

Briefly, the altered method consisted of the following steps: liquid components formic acid and methanol were combined and allowed to react completely in a closed mixing container. After combining the formic acid and methanol, carbon black was added to the mixture prior to addition of the Nylon-66 at a weight ratio as shown in Table 1B. This was accomplished by opening the closed container and adding the required amount of carbon black directly to the liquid dope solvent mixture. Then, Nylon-66 was added to the mixture and the resulting composition was rolled in a jar mill to a maximum temperature of about thirty-four degrees Celsius (34° C.) in a constant temperature bath using a Techne C-85D constant temperature water recirculator, until all nylon was dissolved. The jar was removed from the jar mill. A cap with a sealing arrangement for a propeller shaft was fabricated to minimize volatile losses, and fitted on the jar. The dope was then mixed with a one and one quarter inch three bladed marine propeller attached to a T-line® Model #134-1 laboratory mixer in the same vessel, in an attempt to thoroughly disperse the carbon particles. This second mixing step continued for about 1 hour at about 450 RPM. A small portion (approximately 20 ml) of the dope was subsequently cast and quenched in a laboratory apparatus to simulate the casting process described in U.S. Pat. No. 3,876,738, to produce a single layer, non-reinforced microporous nylon membrane approximately 5 mils in thickness while wet. The membrane was subsequently washed in deionized water, folded over onto itself (to form a structure of approximately 10 mils wet) and dried under conditions of restraint to prevent shrinkage in either the machine direction (x-direction) or cross direction (y-direction). The membrane was found to be strong enough physically to withstand further processing (rinsing, drying, handling, etc), much the same as membrane without carbon added. When the membrane was rubbed vigorously, or when an adhesive tape was applied and removed, no carbon was displaced except that which was trapped in nylon pieces that were physically damaged and removed. Substantially all carbon remained intimately bound to the nylon matrix.

A small sample of dried, double-layer, non-reinforced nylon membrane having a combined thickness of about eight (8) mils after shrinkage (z-direction, after the collapsing wet pore structure was complete) was obtained on which a number of physical measurements were made, as follows:

An initial bubble point ("IBP") and foam-all-over-point ("FAOP") were measured, as described in U.S. Pat. No. 4,645,602, using deionized water as a wet fluid. Mean flow pore ("MFP") tests were undertaken as in ASTM F316-70 and ANSI/ASTM F316-70. Water flow rate measurements of the non-reinforced microporous nylon membrane were performed as described in U.S. Pat. No. 4,473,475. Dry membrane thickness was measured with a ½ inch diameter platen dial thickness indicator gauge (accuracy±0.05 mils (=0.00005 inches)). Fluorescence of the membrane was measured on a Perkin-Elmer LS50B Luminance Spectrophotometer with excitation/emission set at 290/320 nm respectively (excitation/emission slits both set at 2.5 nm). The L (lightness) value was determined using a Macbeth Coloreye 3100 calorimeter. The L-value is part of the CIE L*a*b* standard for colorimetric analysis, one hundred (100) being pure white, and zero (0) being total black. The L-value provides a useful measurement of shades of gray.

MFP, IBP, FAOP and flow were seen to change with the addition of carbon to the formulation in a manner not directly correlatable with the increase in carbon concentration. It is believed that a direct correlation was not seen due to differences in heat build-up during mixing of the dope. It is known that the structure of the dope can be changed by temperature increases above the original formulation temperature (See, U.S. Pat. No. 6,056,529, issued May 2, 2000, the disclosure of which is hereby incorporated by reference). Fluorescence intensity, one the other hand, was correlatable to the concentration of carbon particles in the substrate. A 1:52 carbon:nylon mix substrate was found to exhibit approximately 82.84% less fluorescence than a standard white nylon membrane. A 1:15 carbon:nylon mix substrate was found to exhibit approximately 93.13% less fluorescence than a standard white nylon membrane.

TABLE 1A

| COLOR | FORMIC | METHANOL | NYLON | CARBON |
|---|---|---|---|---|
| Carbon:Nylon White (0:100) % by weight | 76.94% | 7.08% | 15.98% | 0.00% |
| Gray (1:52) % by weight | 76.90% | 6.87% | 15.92% | 0.31% |
| Black (1:15) % by weight | 76.35% | 6.80% | 15.79% | 1.06% |

TABLE 1B

| COLOR (Carbon: Nylon) | MFP (micron) | IBP (psig) | FAOP (psig) | THICKNESS (mils) | FLOW (ml/min) | WHITENESS (L-value) | FLUORESCENCE (intensity) |
|---|---|---|---|---|---|---|---|
| White (0:100) | 0.434 | 43.5 | 48.0 | 7.7 | 49.1 | 98.15 | 0.75 |
| Gray (1:52) | 0.490 | 35.0 | 42.0 | 8.0 | 82.0 | 59.11 | 0.13 |
| Black (1:15) | 0.334 | 48.0 | 55.0 | 9.3 | 35.5 | 35.94 | 0.05 |

Once dried, however, the casts could not be bonded onto a glass slide as a composite. Other casts were made specifically for purposes of bonding to glass. These casts were made using the same dope formulations, equipment and techniques, with the exception of the casting gap, which determines the thickness of the wet casting. A smaller gap was selected, which would produce the thinner single layer. These castings were kept wet and preserved for the lamination step.

The next step of the process, lamination of the wet casts onto glass slides, was initiated by preparing an about 100 mL solution of about 95% ethanol and about 5% water (percent by volume). About 2 mL of 3-aminopropyl-triethoxysilane (made by United Chemicals, Cat. #A0750) was added to the above solution. The combined solution was mixed thoroughly, and was allowed to sit for about five minutes.

Four VWR Brand MicroSlides (part #48300-025) were placed in an evaporating dish and the 3-aminopropyl triethoxysilane solution was poured into the evaporating dish with the four VWR Brand MicroSlides. The four VWR Brand MicroSlides remained submerged in the 3-aminopropyl triethoxysilane solution for about two minutes. To reduce the possibility of contamination, the four VWR Brand MicroSlides were always handled by personnel wearing gloves.

The 3-aminopropyl triethoxysilane solution was drained from the evaporating dish, and ethanol was poured into the evaporating dish in order to rinse the four VWR Brand MicroSlides. The four VWR Brand MicroSlides were then removed from the ethanol solution (with gloved hands) and were blotted dry with a paper towel. During the drying procedure, care was taken not to scratch the surface of the four VWR Brand MicroSlides.

At this time, the four VWR Brand MicroSlides were inspected for visual blemishes or other imperfections. Any of the four VWR Brand MicroSlides with visual blemishes or other imperfections were rejected and not used.

The four VWR Brand MicroSlides were then placed in the evaporating dish and heated in a convection oven at about 120° C. for about ten minutes. The remaining VWR Brand MicroSlides were covered and allowed to cure overnight.

The next day, an about 3.5% solids solution of a polyamido-polyamine epichlorohydrin resin (described in U.S. Pat. No. 4,711,793) was made by adding the following to a 500 mL flask and mixing thoroughly after each step in which a new ingredient was added:
  about 4.4 g NAOH; then
  about 407.5 g DI water; then
  about 87.5 g 20% solids polyamido-polyamine epichlorohydrin resin (specifically 'Resicart E', made by Ciba-Geigy); and then
  about 0.125 g TEPA (tetraethylenepentamine).

The VWR Brand MicroSlides were then submerged in the resin solution for about half an hour. Upon removal of the VWR Brand MicroSlides from the solution, the VWR Brand MicroSlides were rinsed well with DI water and immediately placed on a metal hemi-drum.

Next, the wet-as-cast porous nylon membrane (produced by the lab casting process described above, and as described in U.S. Pat. Nos. 3,876,738 and 4,707,265) was operatively positioned over the VWR Brand MicroSlides and stretched. The wet-as-cast porous nylon membrane was handled by personnel wearing gloves. The wet-as-cast porous nylon membrane used had been cast, quenched, and washed with DI water, but had not yet been exposed to a drying step, hence the term "wet-as-cast." The wet-as-cast porous nylon membrane had a nominal pore size of about 0.2 microns and a target initial bubble point of about 45 PSI (once dried).

DI water was used to rinse the slides to remove any particles from the surface of the wet-as-cast porous nylon membrane/VWR Brand MicroSlide combination. During this process, it was found that leaving a layer of DI water on the VWR Brand MicroSlides before covering with the wet-as-cast porous nylon membrane enhanced the ability to apply and move the membrane around on the VWR Brand MicroSlides and, thus, to remove the air bubbles therebetween.

During the application of the wet-as-cast porous nylon membrane to the treated VWR Brand MicroSlides slide, care was taken to ensure removal of any air bubbles between the wet-as-cast porous nylon membrane and each VWR Brand MicroSlide. The wet-as-cast porous nylon membrane was flattened onto each VWR Brand MicroSlide and all wrinkles were removed. See FIG. 5 for an illustration of this procedure.

Once positioned on the VWR Brand MicroSlides, the wet-as-cast porous nylon membrane was clipped into position with multiple clips applied at regular intervals around the periphery of the hemi-drum. The specific clips were teflon-coated retainer clips, which would not adhere to the membrane after drying, as is known in the art. The entire assembly was then heated in a convection oven at about one hundred twenty degrees Celsius (120° C.) for about one hour. After heating, the excess now dried porous nylon membrane was removed from the VWR Brand MicroSlides by trimming, as is known art.

If the resultant nylon/glass composite slides were to be charge modified, they were then placed inn an evaporating dish, and another, freshly made solution of about 3.5% solids polyamido-polyamine epichlorohydrin resin solution was poured into the evaporating dish with the resultant nylon/glass composite slides.

The resultant nylon/glass composite slides were allowed to remain submerged in the evaporating dish for about five (5) minutes, then removed from the evaporating dish and rinsed with DI water. Most of the excess water was shaken off the resultant nylon/glass composite slides, and the resultant nylon/glass composite slides were placed into a dry evaporating dish and heated until dry in a convection oven at about sixty degrees Celsius (60° C.) for about twenty (20) to about thirty (30) minutes.

The resulting nylon/glass composite slides (charged and uncharged) exhibited a very thin, smooth, layer of porous nylon membrane securely bound to the glass surface. The membrane surface appeared free of deformities, marks or particles.

When the resulting nylon/glass composite slides were tested in DI water, about 0.4M aqueous sodium hydroxide, or about one percent (1%) aqueous sodium dodecyl sulfate (SDS), the nylon portion wetted readily. In general, the bond between the nylon portion and the glass portion of the composite remained strong, and the nylon portion could not be peeled away from the glass portion.

The nylon/glass bond of the resulting nylon/glass composite slides stayed strong even when the nylon/glass composite slides were quickly submerged vertically into boiling solutions of either DI water or SDS. Quick immersion into such boiling solutions does not allow the membrane to wet slowly, and high-pressure air bubbles can develop between the nylon membrane and the glass. Despite the harshness of the treatment, the uncharged glass/nylon composite slides retained their peel strength i.e., the nylon membrane would rip before peeling from the glass.

When the glass/nylon composites produced above were spotted with metanil yellow dye, the nylon membrane exhibited an even coloring throughout the spotted area. The interfaced between the nylon membrane and the glass, because this interface contained the epichlorohydrin resin, became especially strongly colored. Specifically, it is believed that the positive charge of the quaternary amine groups in the polyamido-polyamine epichlorohydrin resin attracted the negatively charged dye molecules even more strongly than the amine groups in the nylon.

As can be seen from the above, this example demonstrates that composite microarray slides useful for carrying a microarray of biological polymers on the surface thereof have been produced using a wet-as-cast nylon membrane and a glass substrate by treating the glass substrate with a surface treatment that facilitates the covalent bonding of the wet-as-cast nylon membrane to the glass substrate in such a manner as to be useful in microarray applications.

As can be seen from Table 1B, the addition of carbon black significantly reduces the fluorescence of the membrane at an excitation/emission of two hundred ninety (290) nm/three hundred twenty (320) nm. The Colorimeter L-Value, which is a measure of whiteness, shows that the addition of carbon black darkens the membrane.

Thus, it is clear that the inventive carbon black impregnated nylon membrane when combined with the inventive surface treatment forms an inventive composite microarray non-luminescent slide composite, the composite having the carbon black impregnated nylon porous membrane effectively attached to the non-porous substrate by covalent bonding such that the combination produced thereby is useful in microarray applications.

Although the carbon black impregnation was effective in reducing fluorescence, it was noticed under magnification that the dispersion of carbon throughout the structure on a microscopic level was less than perfectly uniform. It is expected that further improvements in the mixing and blending of the reagents will improve the uniformity of the dispersion, and therefore the utility of this inventive composite in microarray detection applications.

While the articles, apparatus and methods for making the articles contained herein constitute preferred embodiments of the disclosure, it is to be understood that the disclosure is not limited to these precise articles, apparatus and methods, and that changes may be made therein without departing from the scope of the disclosure which is defined in the appended claims.

What is claimed is:

1. A composite microarray slide, useful for carrying a microarray of biological polymers comprising:
    a substantially non-reflective phase inversion microporous membrane support having both a membrane polymer and a plurality of opaque solids intimately bound to, and/or partially/completely contained within the polymer of the phase inversion membrane support such that the phase inversion microporous membrane support provides little fluorescence from about three hundred (300) nm to about seven hundred (700) nm;
    a non-porous substrate; and
    a surface treatment, operatively positioned between the substantially non-reflective phase inversion microporous membrane support and the non-porous substrate, for sufficiently covalently bonding the non-porous substrate to the substantially non-reflective phase inversion microporous membrane support.

2. The composite microarray slide of claim 1 wherein, the surface treatment comprises:
    a treatment with 3-aminopropyl triethoxysilane followed by treatment with a polyamido-polyamine epichlorohydrin resin.

3. The composite microarray slide of claim 1 wherein, the surface treatment comprises:
    treatment with (10-carbomethoxydecyl) dimethylchlorosilane followed by treatment with a polyamido-polyamine epichlorohydrin resin.

4. The composite microarray slide of claim 1 wherein, the surface treatment comprises:
    treatment with 3-glycidoxypropyltrimethoxysilane.

5. The composite microarray slide of claim 1 wherein, the surface treatment comprises:

treatment with N-(2-aminoethyl)-3-aminopropyltrimethoxysilane followed by treatment with a polyamido-polyamine epichlorohydrin resin.

6. The composite microarray slide of claim 1 wherein, the non-porous substrate comprises a material selected from the group consisting of:

glass, Mylar, ceramic, acrylic, polypropylene, polycarbonate, polysulfone, polyamide and polyaramid.

7. The composite microarray slide of claim 1 wherein, the non-porous substrate comprises:

glass.

8. The composite microarray slide of claim 1 wherein, the non-porous substrate comprises:

a polyester.

9. The composite microarray slide of claim 1 wherein, the non-porous substrate comprises:

Mylar.

10. The composite microarray slide of claim 1 wherein the substantially non-reflective phase inversion microporous membrane support comprises a material selected from the group consisting of:

Nylon 66, Nylon 46, Nylon 6, polysulfone, polyethersulfone, polyvinylidenediflouride (PVDF).

11. The composite microarray slide of claim 1, wherein the substantially non-reflective phase inversion microporous membrane support comprises:

polyamides.

12. The composite microarray slide of claim 1 wherein the opaque solids comprise:

pigments.

13. The composite microarray slide of claim 1 wherein the opaque solids comprise:

carbon particles.

14. The composite microarray slide of claim 1 wherein the substantially non-reflective phase inversion microporous membrane support has been charge-modified.

15. The composite microarray slide of claim 13 wherein the carbon particles are less than five microns in size.

16. The composite microarray slide of claim 13 wherein the carbon particles are substantially uniformly distributed throughout the substantially non-reflective phase inversion microporous membrane support.

17. The composite microarray slide of claim 13 wherein the carbon particles are incorporated into the substantially non-reflective phase inversion microporous membrane/support.

18. The composite microarray slide of claim 1 wherein the surface treatment comprises:

treatment with an organosilane having the formula:

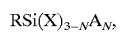

where X is an ethoxy, methoxy, or chloride group, and R is a functional group that with nylon, or with an intermediate substance capable of bonding to nylon and 'A' group is an additional unreactive group that may or may not be present (depending on whether N is 0, 1, or 2).

19. The composite microarray slide of claim 1 wherein, the surface treatment comprises:

treatment with 2(3,4-epoxycyclohexyl)-ethyltrimethoxysilane.

* * * * *